United States Patent
Schramm et al.

(10) Patent No.: US 8,884,000 B2
(45) Date of Patent: Nov. 11, 2014

(54) SAPORIN-L1 INHIBITORS AND USES THEREOF

(75) Inventors: Vern L. Schramm, New Rochelle, NY (US); Gary Brian Evans, Lower Hutt (NZ); Peter Charles Tyler, Wellington (NZ); Jennifer Mary Mason, Petone (NZ)

(73) Assignees: Albert Einstein College of Medicine of Yeshiva University, Bronx, NY (US); Industrial Research Limited, Lower Hutt (NZ)

( * ) Notice: Subject to any disclaimer, the term of this patent is extended or adjusted under 35 U.S.C. 154(b) by 342 days.

(21) Appl. No.: 12/932,051

(22) Filed: Feb. 15, 2011

(65) Prior Publication Data

US 2011/0201674 A1    Aug. 18, 2011

Related U.S. Application Data

(60) Provisional application No. 61/338,376, filed on Feb. 17, 2010.

(51) Int. Cl.
  C07H 21/02    (2006.01)
  C07H 21/04    (2006.01)
  C12Q 1/68     (2006.01)

(52) U.S. Cl.
  USPC .............. 536/25.6; 435/6; 435/184; 536/23.1; 536/26.3

(58) Field of Classification Search
  USPC ................. 435/6, 375, 184; 514/1, 2, 44, 47; 424/9.1; 536/1.11, 23.1, 25.6, 26.3
  See application file for complete search history.

(56) References Cited

U.S. PATENT DOCUMENTS

| | | |
|---|---|---|
| 5,736,536 A | 4/1998 | Siegall et al. |
| 7,777,025 B2 | 8/2010 | Schramm et al. |
| 2011/0053146 A1 | 3/2011 | Schramm et al. |
| 2011/0136106 A1 | 6/2011 | Schramm |

FOREIGN PATENT DOCUMENTS

| | | |
|---|---|---|
| WO | WO 2008/105796 A2 | 9/2008 |
| WO | WO 2010/053498 A2 | 5/2010 |

OTHER PUBLICATIONS

Sturm et al, Biochemistry, vol. 48, No. 41, pp. 9941-9948 (2009).*
Ho, M-C. et al., Proc. Nat'l. Acad. Sci., vol. 106, No. 48, pp. 20,276-20,281 (2009).*
Ho, Meng-Chiao et al., entitled "Transition state analogues in structures of ricin and saporin ribosome-inactivating proteins," PNAS, vol. 106, No. 48, Dec. 1, 2009, 20276-20281; and Supporting Information (13 pages).
Roday, Setu et al., entitled "Vinyl-Deoxyadenosine in a Sarcin/Ricin RNA Loop and its Binding to Ricin Toxin A-Chain," Biochemistry, May 29, 2007;46(21):6169-6182.
Sturm, Matthew B et al., entitled "Circular DNA and DNA/RNA Hybrid Molecules as Scaffolds for Ricin Inhibitor Design," J Am Chem Soc, May 2, 2007;129(17):5544-5550.
Sturm, Matthew B et al., entitled "Detecting Ricin: A Sensitive Luminescent Assay for Ricin A-chain Ribosome Depurination Kinetics," Anal Chem, Apr. 15, 2009; 81(8):2847-2853.
Strum, Matthew B et al., entitled "Transition State Analogues Rescue Ribosomes from Saporin-L1 Ribosome Inactivating Protein," Biochemistry, Oct. 20, 2009; 48(41): 9941-9948, and Supporting Information (7 pages).

* cited by examiner

*Primary Examiner* — Jane Zara
(74) *Attorney, Agent, or Firm* — Amster, Rothstein & Ebenstein LLP

(57) ABSTRACT

Inhibitors of saporin-L1 are disclosed, as are related compositions and uses thereof, in particular in cancer therapy that employs saporin-L1-linked immunotoxins.

16 Claims, 6 Drawing Sheets

SAPORIN-L1 INHIBITORS AND USES THEREOF

CROSS-REFERENCE TO RELATED APPLICATION

This application claims the benefit of U.S. Provisional Patent Application No. 61/338,376, filed on Feb. 17, 2010, the content of which is herein incorporated by reference.

STATEMENT OF GOVERNMENT SUPPORT

This invention was made with government support under grant number CA 072444 awarded by the National Institutes of Health, U.S. Department of Health and Human Services. The government has certain rights in the invention.

FIELD OF THE INVENTION

The present invention relates to inhibitors of saporin-L1 and related compositions and uses thereof, in particular in cancer therapy that employs saporin-L1-linked immunotoxins.

BACKGROUND OF THE INVENTION

Throughout this application various publications are referred to in parentheses. Full citations for these references may be found at the end of the specification immediately preceding the claims. The disclosures of these publications are hereby incorporated by reference in their entireties into the subject application to more fully describe the art to which the subject application pertains.

Ribosome inactivating proteins (RIPs) are N-glycohydrolases that catalyze the depurination of adenosine $A_{4234}$ from the highly conserved sarcin-ricin loop of the 28S eukaryotic ribosomal subunit RNA (1). Depurination inhibits the binding of elongation factor 2 to the ribosome, halts protein synthesis, and causes cell death (2). RIPs with broad polynucleotide:adenosine glycosidase activity can target other ribosomal sites and non-ribosomal substrates, including DNA, RNA and poly(A) (3, 4). Saporin-L1 toxin, a RIP from the leaves of the *Saponaria officinalis* plant can release adenine from poly(A), herring sperm DNA, tRNA, *Escherichia coli* rRNA, and globin mRNA at physiologic pH (5, 6). Fifteen saporin isoforms have been characterized from *Saponaria officinalis* including 9 seed, 3 leaf, and 3 root RIPs. These isoforms differ in ribosome translation inhibition activities and nascent cellular toxicity (7). Analysis of 50 type I and II RIPs revealed only saporin-L1 with the ability to release adenine from RNA of MS2, TMV, and AMCV viruses at physiologic pH, a catalytic activity unique in the RIP family of enzymes (3).

Transition state structures have been solved for the ricin A-chain, a potent RIP from castor beans (8, 9, 10). Kinetic isotope effect studies established that ricin A-chain hydrolysis of 10-mer RNA and DNA stem-loop substrates occurs through leaving group activation and forms ribooxacarbenium ion transition states (9, 10). Small RNA stem-loops are substrates for RIPs, and stem-loop substrate mimics of the sarcin-ricin loop serve as inhibitor scaffolds. Substrate stem-loops contain a GAGA tetraloop for RIP recognition and alternating C-G base pairs for stem stability and loop folding. Transition state analogues for ricin A-chain featured protonated 1-aza sugars to mimic the oxacarbenium ion intermediate and leaving groups with an elevated $pK_a$ at the depurination site (8). Ricin A-chain shows robust catalytic activity on stem-loop RNA substrates at pH 4 but is inactive with these substrates at neutral pH. Transition state analogues of ricin A-chain are nanomolar inhibitors at pH 4 but do not protect ribosomes from ricin A-chain action at neutral pH.

Ribosome inactivating proteins have potential as anticancer agents when linked to an appropriate recognition motif (11). Powerful inhibitors of the RIP can then provide a rescue agent to prevent the post-therapy vascular leak syndrome commonly associated with RIP immunochemotherapy (12). Such inhibitors could provide extracellular protection against circulating toxins. The present invention addresses the need for providing inhibitors of ribosome inactivating proteins that function at physiological pH and that can be used in cancer therapy that employs saporin-L1-linked immunotoxins.

SUMMARY OF THE INVENTION

The present invention provides small, stable and tight-binding transition state inhibitors of saporin-L1 that are effective at physiological pH, and pharmaceutical compositions comprising the inhibitors and a pharmaceutically acceptable carrier.

The invention also provides a method for inhibiting the activity of saporin-L1 comprising contacting saporin-L1 with any of the saporin-L1 inhibitors disclosed herein.

The invention further provides a method for treating or preventing a side effect in a subject undergoing chemotherapy with saporin-L1 attached to a targeting agent, the method comprising administering to the subject a therapeutically effective amount of any of the inhibitors of saporin-L1 disclosed herein.

DETAILED DESCRIPTION OF THE INVENTION

The invention provides a transition state inhibitor of saporin-L1 selected from the group consisting of:

i) an inhibitor comprising the structure:

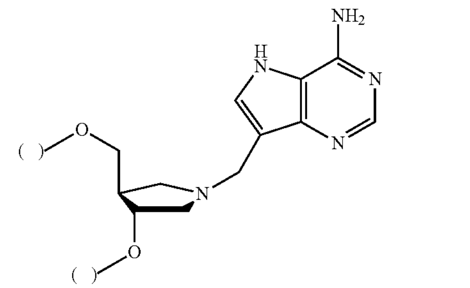

where ( ) represents the point of attachment to G;

ii) an inhibitor having the structure:

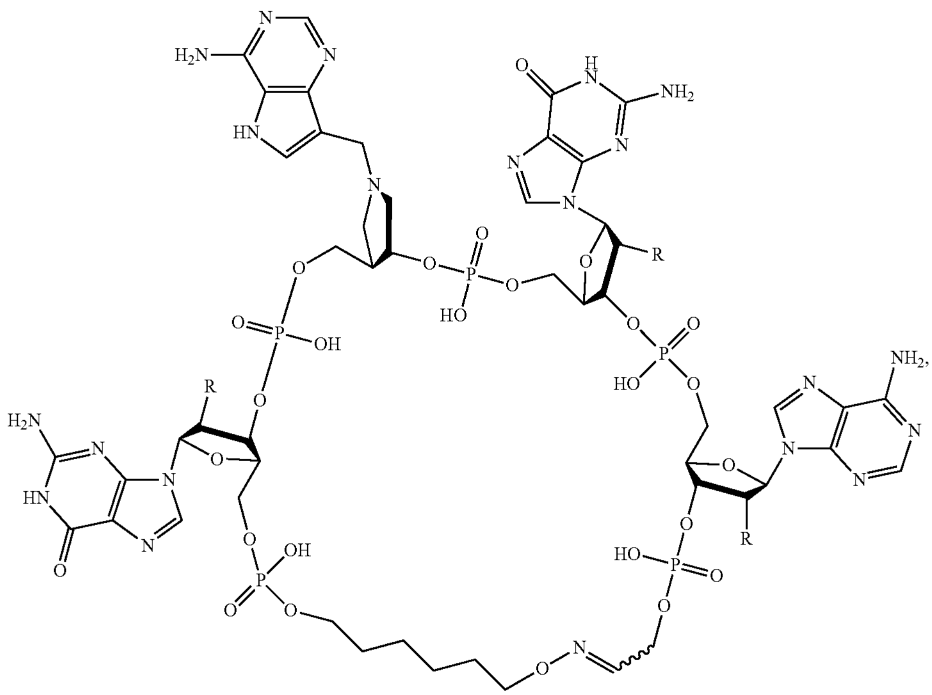

I G

G A $X_1$-$X_{1'}$ $X_2$-$X_{2'}$ $X_3$-$X_{3'}$

5' 3' wherein $X_1$-$X_{1'}$, $X_2$-$X_{2'}$, and $X_3$-$X_{3'}$ are independently C-G, G-C, A-T, T-A, U-A, or A-U, or an analogue thereof, or any base-paired nucleotides or their analogues that form a stable stem-loop nucleic acid structure; wherein A, C and G are independently DNA, RNA, or RNA containing a 2'-$OCH_3$ substitution; wherein U can contain a T-$OCH_3$ substitution; and wherein I is wherein each R is independently $OCH_3$ or aryl or alkyl, where the aryl or alkyl can be optionally substituted with one or more of OH, =O, $OCH_3$, $NH_2$, C1-C6 alkyl or halogen;

iii) an inhibitor having the structure:

iv) an inhibitor having the structure:

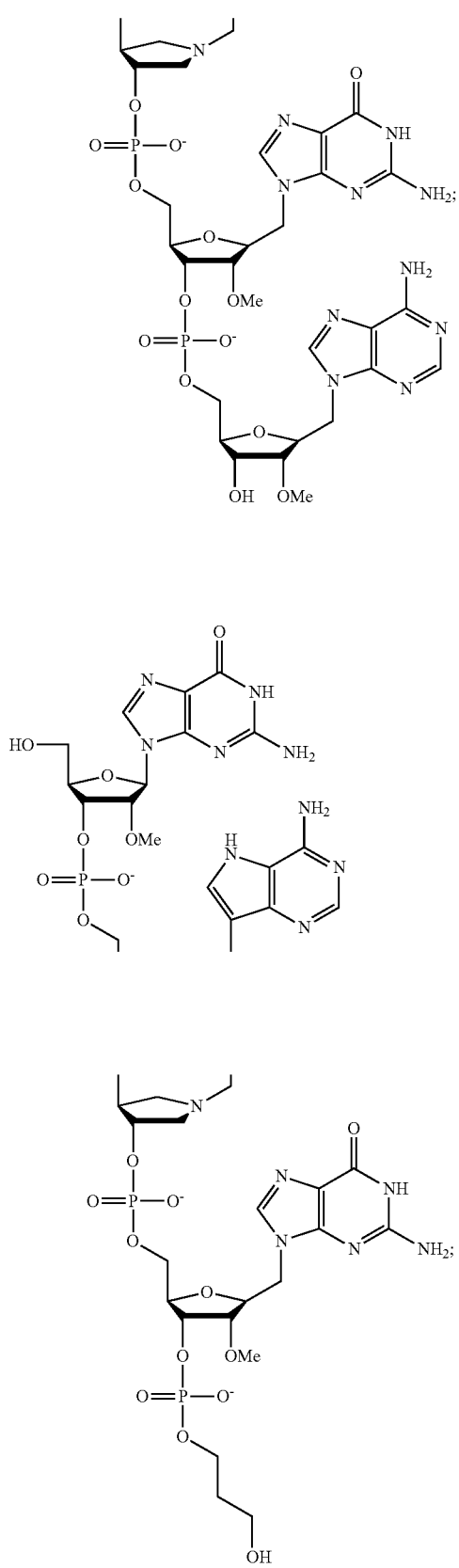
v) an inhibitor having the structure:
vi) an inhibitor having the structure:
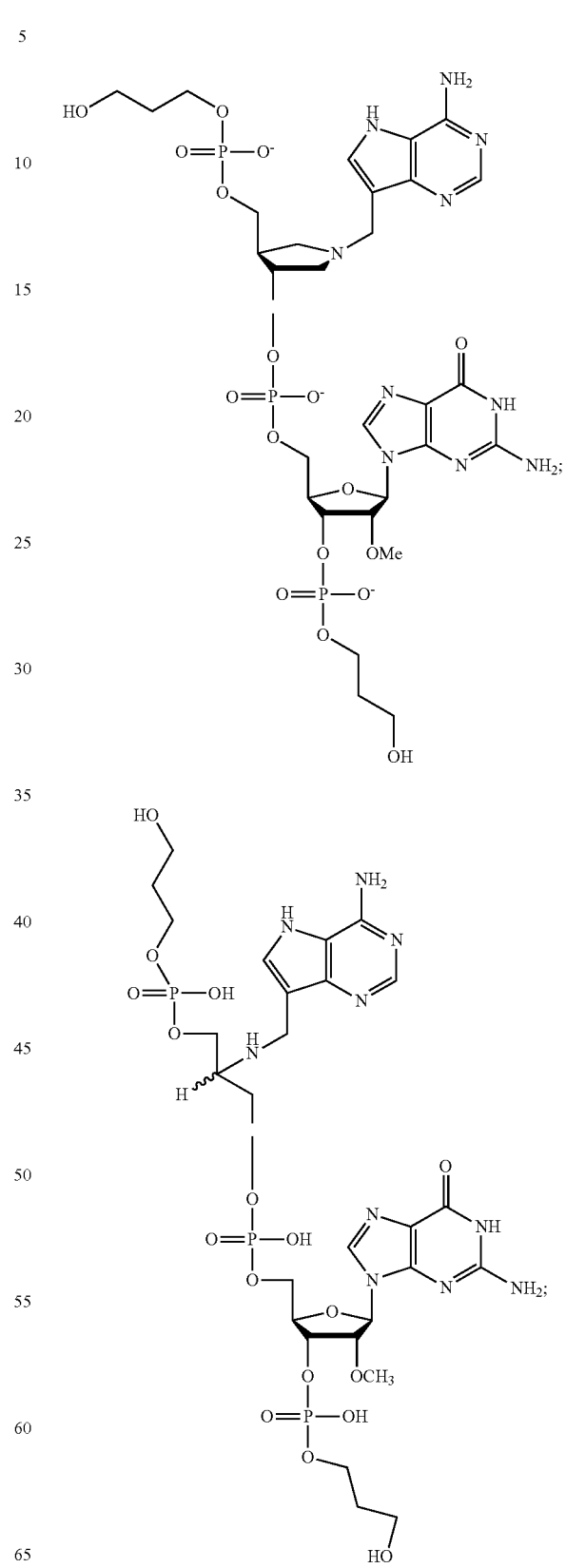

vii) an inhibitor having the structure:

and viii) an inhibitor having the structure:

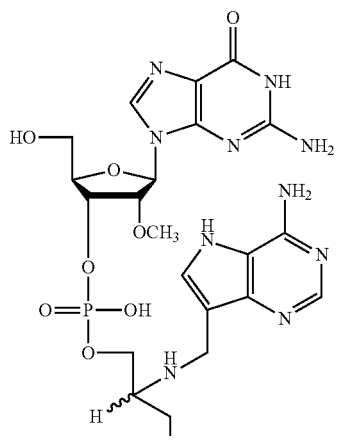

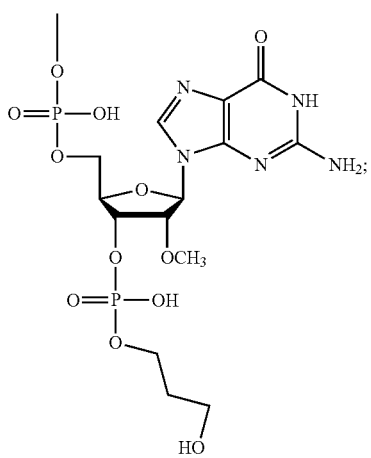

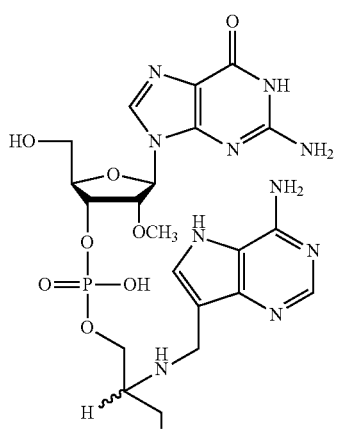

-continued

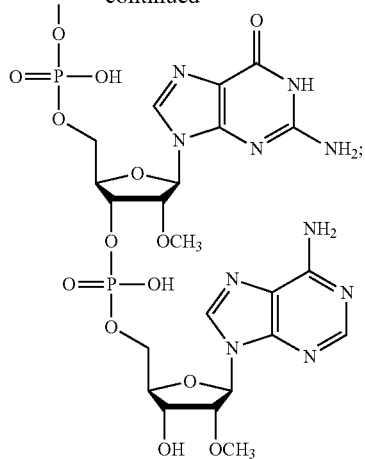

or a pharmaceutically acceptable salt of any of inhibitors i)-viii).

The inhibitor comprising the structure:

```
      I G
      G A
     X₁-X₁'
     X₂-X₂'
     X₃-X₃'
     5'   3'
``` can comprise, for example, additional X-X, pairs wherein in each pair, X and X, are independently C-G, G-C, A-T, T-A, U-A, or A-U, or an analogue thereof, or any base-paired nucleotides or their analogues that form a stable stem-loop nucleic acid structure; wherein A, C and G are independently DNA, RNA, or RNA containing a 2'-OCH₃ substitution; and wherein U can contain a 2'-OCH₃ substitution. The inhibitor can comprise, for example, X₄-X₄', or X₄-X₄' and X₅-X₅'. The inhibitor can consist or consist essentially of the structure.

The inhibitor can, for example, comprise or have the structure:

```
      I G          or        I G
      G A                    G A
      C-G                    C-G
      G-C                    G-C
      C-G                    C-G
      5'   3'                G-C
                             C-G
                             5'   3'.
```

"A" represent the nucleotide adenylate (in RNA) or deoxyadenylate (in DNA). "C" represents the nucleotide cytidylate (in RNA) or deoxycytidylate (in DNA). "G" represents the nucleotide guanylate (in RNA) or deoxyguanylate (in DNA). "T" represent the nucleotide thymidylate in DNA. "U" represents the nucleotide uridylate in RNA. In one embodiment, A, C and G are DNA. In another embodiment, A, C and G are RNA. In DNA, hydrogen (H) is attached to the 2' carbon of the pentose (i.e., 2-deoxyribose). In RNA, H and —OH are attached to the 2' carbon of the pentose (i.e., ribose). In one embodiment of the invention, at least one A, C or G is RNA and contains a —OCH$_3$ (i.e., —OMe or —OMethyl) substitution at the 2' carbon of the pentose ring.

In inhibitor structure ii), R is OCH$_3$ or an aryl or alkyl protecting group to prevent the action of ribonuclease degradation of the inhibitor. Preferably, the alkyl is C1-C6 alkyl, and more preferably, C1-C3 alkyl. Preferably, the aryl is phenyl or a phenyl substituted with one or more of —CH$_3$, —OH, —OCH$_3$, —F, —Cl, —Br, or —I.

Figure 1:
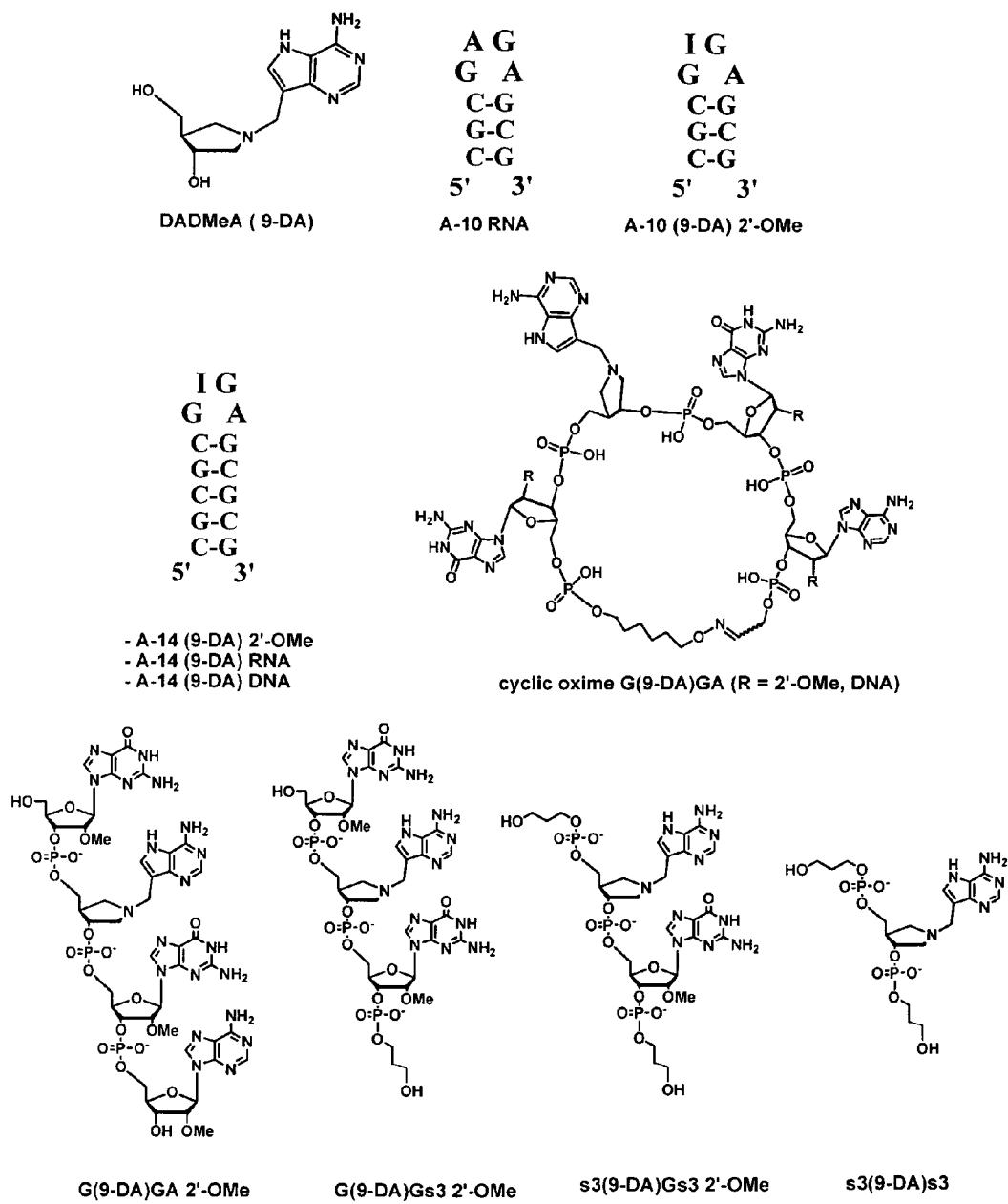
FIG. 1. Substrate and inhibitor constructs for saporin-L1 assays and inhibition. Top: Transition state mimic DADMeA (9-DA), a 9-deazaadenine N-hydroxypyrrolidine sugar. A-10 RNA (SEQ ID NO:1) stem-loop substrate contains the GAGA tetraloop motif and alternating C-G base pairs for stem structure and loop folding. A-10 (9-DA) 2'-OMe contains DADMeA at the target RIP depurination site of the GAGA tetraloop and contains 2'-OMe modified bases (excluding DADMeA). Middle: Three 14-mer constructs containing DADMeA including A-14 (9-DA) 2'-OMe, RNA, or DNA scaffolds. Cyclic oxime G(9-DA)GA 2'-OMe or DNA constructs are tetramers with 5'- to 3'-oligonucleotide ends closed by a synthetic linker (16). Bottom: Linear inhibitor. Tetramer G(9-DA)GA 2'-OMe, trimer G(9-DA)Gs3 2'-OMe, dimer s3(9-DA)Gs3 2'-OMe and monomer s3(9-DA)s3 where s3 denotes a propyl phosphate.

Preferred inhibitors include those illustrated in FIG. 1 and listed in Table 3 (first 9 compounds in Table 3).

The present invention also provides a pharmaceutically acceptable salt of any of the inhibitors disclosed herein. Pharmaceutically acceptable salts include non-toxic salts derived from inorganic or organic acids, such as, for example, the following salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

The invention also provides a pharmaceutical composition comprising any of the inhibitors disclosed herein and a pharmaceutically acceptable carrier. As used herein, a "pharmaceutically acceptable" carrier means a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, sterile isotonic saline, water, and emulsions such as, for example, oil/water emulsions and microemulsions.

The invention also provides a method for inhibiting the activity of saporin-L1 comprising contacting saporin-L1 with any of the inhibitors disclosed herein. The present inhibitors are active at physiological pH. Accordingly, the method can be carried out at a pH of 7.3-7.5. The method can be carried out, for example, in a subject who has been poisoned with saporin-L1 toxin.

The invention further provides a method for treating or preventing a side effect in a subject undergoing chemotherapy with saporin-L1 linked or attached to a targeting agent, the method comprising administering to the subject a therapeutically effective amount of any of the inhibitors of saporin-L1 disclosed herein. Saproin-L1 can be linked or attached to a targeting agent such as an antibody, antibody fragment (e.g., F(ab')$_2$ or Fab' fragment), peptide or nucleic acid aptamer, and used to treat a disease such as cancer. The side effect can be associated with vascular leak syndrome (VLS). VLS can occur following introduction of saprorin-L1 into the circulation, which could occur for example following tumor lysis. Increased vascular permeability in VLS results in extravasation of fluids and proteins. The side effect can be one or more of fluid retention, increase in body weight, hypotension, peripheral edema, ascites, hypoalbuminemia, oliguria, dyspnea, respiratory insufficiency, pleural or pericardial effusion, or in severe cases pulmonary or cardiovascular failure. Administration of the inhibitors of saporin-L1 described herein can be used to prevent or treat vascular leak syndrome in a subject undergoing chemotherapy with a saporin-L1-linked immunotoxin for treatment of cancer. As used herein, to "treat" a side effect means to minimize or reverse the side effect.

The inhibitors of the present invention can be administered to subjects using routes of administration known in the art. The administration can be systemic or localized to a tumor site. Routes of administration include, but are not limited to, intravenous, intramuscular, intrathecal or subcutaneous injection, oral or rectal administration, and injection into a tumor site. Intravascular administration is a preferred route of administration.

The subject is preferably a mammal and most preferably a human.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Introduction

Saporin-L1 has not been kinetically characterized with small substrates or inhibitors. Here its kinetic properties are characterized on small stem-loop substrates and on mammalian ribosomes, and novel transition state analogue inhibitors are provided, all which function at physiological pH values. Kinetic analysis takes advantage of a sensitive and continuous assay for adenine linked to luciferase-based light production (13). Saporin-L1 catalyzes the depurination of adenines from A-10 (an RNA stem-loop 5'-CGCGA̲GAGCG-3' (SEQ ID NO:1) mimic of the sarcin-ricin loop), linear and covalently closed circular constructs related to A-10, and mammalian 80s ribosomes, all at physiologic pH. The transition state (TS) mimic 9-deazaadenine-9-methylene-N-hydroxypyrrolidine (DADMeA) replacement for adenosine in the RIP recognition GA̲GA tetraloop motif inhibits saporin-L1 catalysis. Inhibitors were synthesized against saporin-L1, including monomer to 14-mer oligonucleotides, employing the DADMeA transition state mimic. Stem-loop inhibitor constructs, cyclic tetramer 5'- to 3'-covalently closed circular GAGA tetraloops, and monomeric inhibitors were also applied to saporin-L1. A minimal saporin-L1 inhibitor scaffold with 2'-OMe containing compounds designed to give enhanced nuclease stability provided inhibition of saporin-L1 to low nanomolar K$_i$ values and also protected ribosomes from saporin-L1 action in rabbit reticulocyte lysates.

Materials and Methods

Materials. Oligonucleotide A-10 was purchased from Dharmacon (Lafayette, Colo.). 5'-DMT protected 9-DA azasugar was synthesized and purified as previously described (8). DNA/RNA synthesis reagents were purchased from Glen Research (Sterling, Va.) and ChemGene Co. (Ashland, Mass.). HPLC purifications were preformed on a Waters 626 pump with a 996 photodiode array detector with Millennium software. Firefly luciferase ATP assay kit (ATPlite) was purchased from Perkin Elmer (Waltham, Mass.). Phosphatase inhibitors (PhosSTOP) were purchased from Roche Applied Science (Indianapolis, Ind.). RNase inhibitor (SuperRNasin) was purchased from Ambion (Austin, Tex.). Ricin A-chain and Saporin-S6 was purchased from Aldrich Chemical Corp.

(Ashland, Mass.). For translation assays, FlexiRabbit Reticulocyte Lysate System, luciferase assay system, and rabbit reticulocyte lysate (untreated) were purchased from Promega (Madison, Wis.). Buffers and enzyme preparations were checked for RNase activity using RNaseAlert from Ambion (Austin, Tex.). DEPC treated water (0.1% DEPC stirred for 20 min followed by 30 min autoclave treatment) was used in all enzymatic reactions and buffers. All other reagents used were purchased in the highest purity available from Fisher Scientific (Pittsburgh, Pa.) or Aldrich Chemical Corp. (Ashland, Mass.). Concentrations of adenine and oligonucleotides were measured using a Nanoprop 1000 (Thermo Fisher Scientific, Waltham, Mass.). Inhibitor concentrations were determined spectrophotometrically including the published millimolar extinction coefficient of 8.5 at 275 nm at pH 7 for 9-deazaadenosine (14). Enzyme concentrations of saporin-L1 and saporin-S6 were determined with the BCA protein assay kit from Pierce (Rockford, Ill.). Luminescence measurements were accomplished on a GloMax 96-well luminometer from Promega (Madison, Wis.).

Saporin-L1 Isolation. Saporin-L1 was isolated from the leaves of *Saponaria officinalis* (common soapwort) as described previously with modifications described below (7). Freshly harvested leaves (10 g) were frozen and ground with a pestle under liquid nitrogen. The powder was suspended in 80 mL extraction buffer (10 mM $Na_2HPO_4$ (pH 5.5) (titrated with citric acid), 175 mM NaCl, 2.5 mM $MgCl_2$, 1 mM $CaCl_2$, one tablet of complete protease inhibitor (Roche), 1% (w/v) poly(vinylpolypyrrolidone), 1% cellulase, 0.5% hemicellulase, and 150 units pectinase). The mixture was stirred at room temperature for 3 hours and then acidified to pH 4.0 with acetic acid. Triton X-100 was added to 0.5% (v/v) and the mixture was stirred for an additional 1 hour. The digested and lysed leaf mixture was then filtered through cheese cloth and centrifuged at 25,000 g for 30 minutes. The supernatant was loaded on SP-sepharose FF resin (Amersham) pre-equilibrated in 10 mM sodium phosphate, pH 4.5. The column was extensively washed with 10 mM sodium phosphate pH 7.4 and the crude saporin-L1 containing fraction was eluted with the same buffer containing 1 M NaCl. The elute was dialyzed against 10 mM sodium phosphate pH 7.4 titrated to pH 4.5 with acetic acid and loaded onto carboxymethyl-FF (three 1 mL columns, Amersham) pre-equilibrated in buffer [10 mM sodium phosphate pH 7.4]. The columns were washed extensively with buffer to achieve pH equilibration. Saporin-L1 was eluted with a 50 min linear gradient of 0-300 mM NaCl in 10 mM sodium phosphate pH 7.4 at 1 ml/min and was identified as an ~30 kD band by sodium dodecyl sulfate-polyacrylamide gel electrophoresis (SDS-PAGE). Saporin-L1 fractions were combined, titrated to pH 4.5 with acetic acid, and loaded onto heparin HP (three 1 mL columns, Amersham) pre-equilibrated in buffer. Saporin-L1 was eluted with a 50 minute linear gradient of 0-800 mM NaCl in 10 mM sodium phosphate pH 7.4 (1 ml/min). Saporin-L1 was eluted as the last major peak in the chromatogram and was identified by SDS-PAGE. The >80% pure Saporin-L1 was concentrated by spin Amicon concentrator and purified to >95% homogeneity with a BioSep-SEC-S 2000 column (Phenomenex) equilibrated in 20 mM sodium phosphate pH 7.4 and eluted at 1 mL/min. The gel filtration purification step was needed to remove trace DNAase and RNAase activities from Saporin-L1. Saporin-L1 was concentrated to ~1 mg/mL and stored at 4° C. The yield was ~0.5 mg saporin-L1 from 10 g of leaf material. Commercial saporin-S6 was purified with the heparin chromatography step as described above.

Saporin-L1 Seed Isolation. 50 g of *Saponaria officinalis* (common soapwort) seeds were frozen in liquid nitrogen and ground to a powder in a seed grinder. The powder was added to 350 mL of PBS and stirred overnight at 4° C. The mixture was filtered through cheese cloth, centrifuged at 25,000 g for 30 minutes, and extensively dialyzed against 10 mM $Na_2HPO_4/NaH_2PO_4$ pH 7.0. The cloudy solution was acidified to pH 4.5 with acetic acid, and clarified with centrifugation at 5000 g for 10 minutes. The supernatant was collected and loaded onto a heparin column (20 mL Amersham) and crude SAP-L1 was eluted in the end fractions with a gradient of 0-500 mM NaCl in 10 mM $Na_2HPO_4/NaH_2PO_4$ pH 7.4 over 17 columns. Because SAP-L1 was a minor protein within the seed preparations with similar migration on SDS-Page to seed isoforms, the fastest catalyzing fractions of 50 μM A-10 RNA substrate (containing SAP-L1) were also identified by an activity based assay using the adenine lucifease assay for adenine quantification. Crude SAP-L1 was concentrated in an Amicon, dialyzed against 10 mM $Na_2HPO_4/NaH_2PO_4$ pH 7.4 and further purified as described for leaf derived protein. Final isolation yields were 1 mg of saporin-L1 per 50 grams of seed.

Saporin-L1 N-terminal Sequencing and Mass Analysis. Purified saporin-L1 from the leaves of *Saponaria officinalis* was verified by N-terminal sequencing at the Rockefeller University Proteomics Resource Center (New York, N. Y.). The N-terminal sequence was VIIYELNLQG (SEQ ID NO:2), which matched previous reports for the Saporin-L1 isoform (7). The mass of saporin-L1 was measured on a MALDI-TOF mass spectrometer in the linear positive ion mode with external calibration. Protein samples (~20 μM) were desalted with a ZipTip (Waters) as described by the manufacturer and eluted onto a 100 well gold plate with 1 μL of matrix solution (20 mg/mL sinapic acid in 70% acetonitrile/$H_2O$ with 0.1% TFA). The mass of saporin-L1 (28,749 Da) isolated from the leaves of *Saponaria officinalis* was comparable to previous reported masses for saporin-L1 leaf and vacuolar isoforms (28,740 to 28,765 Da) (15).

Synthesis of Oligonucleotides Inhibitors. Cyclic oligonucleotides and 1-aza sugar phosphoramidites were synthesized and purified as reported previously (16). Stem-loop oligonucleotides were synthesized on a 1 μmol scale with DMT-on mode using an Expedite 8909 DNA/RNA synthesizer following standard synthesis protocols for β-cyanoethyl phosphoramidite chemistry with acetyl protected cytosine phosphoramidite and 5-benzylthio-1H-tetrazole as activator. Cleavage from solid support and base deprotection of a 1 μmol synthesis was accomplished in 1.5 mL AMA reagent (1:1 concentrated $NH_4OH$ to 40% aqueous methylamine) for 45 minutes at 37° C. The reaction mixture was centrifuged, the supernatant collected, and the resin was washed twice with 3:1:1 ethanol:acetonitrile:water. Combined supernatant and washes were evaporated to dryness under vacuum. 2'-O-TBDMS deprotection of the A-14 (DADMeA) RNA (1 μmole) was accomplished using 250 μL of anhydrous TEA HF/NMP solution (1.5 mL of N-methylpyrrolidinone, 750 μL of TEA, and 1.0 mL of TEA-3HF) heated to 65° C. for 2 h (17). This reaction mixture was diluted with 2 mL of 0.5 M $NH_4OAc$ and evaporated to dryness under vacuum.

HPLC purification of the 5'-trityl stem-loop oligonucleotides was accomplished to >95% purity on a Waters Delta-Pak (7.9 mm×300 mm) semipreparative C18 reversed phase column at 3.5 mL/min in 20 mM $NH_4OAc$/5% $CH_3CN$ with a linear 0-40% gradient of $CH_3CN$ in 25 min. Trityl protected oligonucleotides were the major peak and eluted at ~25 min. The major late eluting fraction was evaporated to dryness under vacuum. The pellet was dissolved in 1 mL of 80% acetic acid in water, incubated at 30° C. for 1 hour, and the solution was evaporated to dryness under vacuum. HPLC purification of the final oligonucleotide was accomplished to >95% purity on a Waters Delta-Pak (7.9 mm×300 mm) semi-preparative C18 reversed phase column at 3.5 mL/min in 50 mM triethyl ammonium acetate pH 7.0 with a linear 0-80% gradient of 50% aqueous methanol in 40 min. The final product was evaporated to dryness in a speed vac concentrator and resuspended in sterile RNAase free water.

Linear inhibitors were synthesized in DMT-off mode on an Expedite 8909 synthesizer in otherwise identical conditions to stem-loop oligonucleotides. After deprotection in AMA, the oligonucleotides were purified by HPLC to >95% purity as described for stem-loops in 50 mM triethyl ammonium acetate pH 7.0 with a linear 0-50% gradient of 50% aqueous methanol in 40 to 60 min.

Stem-loop, cyclic, and linear oligonucleotide structures were confirmed using a MALDI-TOF mass spectrometer as described previously (16). Observed and calculated masses for the final compounds are indicated in Table 1. Prior to use in inhibition assays, stem-loop oligonucleotides were heated to 95° C. for 1 minute and cooled on ice.

TABLE 1

MALDI-TOF Results for Oligonucleotides

| Oligonucleotide | Calculated Mass | Observed Mass |
| --- | --- | --- |
| A-10 | 3238.1 | 3237.9 |
| linear GAGA | 1286.9 | 1288.7 |
| cyclic GAGA | 1585.3 | 1585.9 |
| A-14 (9-DA) 2'-OMe | 4686.4 | 4685.3 |
| A-14 (9-DA) RNA | 4534.9 | 4535.5 |
| A-14 (9-DA) DNA | 4326.9 | 4327.7 |
| A-10 (9-DA) 2'-OMe | 3330.8 | 3331.2 |
| cyclic oxime (9-DA) 2'-OMe | 1623.4 | 1624.9 |
| cyclic oxime (9-DA) DNA | 1533.3 | 1534.5 |
| G(9-DA)GA 2'-OMe | 1324.3 | 1325.1 |
| G(9-DA)Gs3 2'-OMe | 1119.3 | 1120.1 |
| s3(9-DA)Gs3 2'-OMe | 898.2 | 901.0 |

Saporin-L1 Kinetic Assay. Saporin-L1 kinetics on substrate A-10 RNA (5'-CGCGAGAGCG-3') (SEQ ID NO:1) were determined using a continuous coupled assay for quantifying free adenine by linking it to the production of light from luciferase (13). In brief, an adenine detection buffer was prepared in bulk (50 mL of charcoal-filtered solution containing 100 mM tris-acetate pH 7.7, 2 mM phosphoenolpyruvic acid, 2 mM sodium pyrophosphate, 2 mM 5-phospho-D-ribosyl-1-pyrophosphate (PRPP), 15 mM $NH_4SO_4$, 15 mM $(NH_4)_2MoO_4$, and phosphatase inhibitors in RNAase free water) and stored at −80° C. in 1 mL aliquots. Prior to use in adenine assays, coupling enzymes were prepared by adding 10 mM $MgSO_4$, 8 units of APRTase, 8 units of phosphoenolpyruvate dikinase, 200 µL D-luciferin/luciferase (ATPLite) reagent and 1 µL of SuperRNasin (Ambion) per 1 mL of coupling enzymes buffer. One unit of enzyme activity was defined as the amount that forms one mole of product per min at 20° C.

Varying concentrations of A-10 RNA (5'-CGCGAGAGCG-3') (SEQ ID NO:1) were prepared in 1:1 diluted coupling enzymes in a 96-well luminometer plate and reactions were initiated with 300 µM saporin-L1 (50 µL total reaction). Luminescence was measured with a luminometer in kinetic acquisition mode for several minutes. Adenine standards were prepared in identical assay conditions. The initial rates of adenine formation were calculated by converting luminescent rate (lumens/second) to enzymatic rate (pmol adenine/min/pmol enzyme) calibrated from the adenine standard curve. Kinetic parameters $k_{cat}$ and $K_m$ were calculated by fitting initial rates to the Michaelis-Menten equation.

Rabbit ribosomes (80S) were purified from rabbit reticulocyte lysate by sucrose cushion centrifugation (13). Saporin-L1 (300 µM) was analyzed for kinetic parameters with ribosomes as substrate as described for A-10 RNA substrate. Ribosome concentration was determined by depurinating (to completion) two stock concentrations with 500 nM RTA and comparing the final luminescence to the adenine standard curve fit. RTA releases 1 mol adenine from 1 mol ribosome and thus provides a method of quantitation.

Saporin-L1 Inhibition Assays. Saporin-L1 inhibition constants for stem-loop, circular, and linear oligonucleotides were determined in a competition assay using RNA A-10 substrate with quantitative analysis of adenine release as described for kinetic assays. Varying concentrations of inhibitor were pre-incubated with 300 µM saporin-L1 for 10 min in 1× continuous assay buffer at 20° C. Reactions were initiated by the addition of A-10 (−80 µM) and light generation (RLU) was measured in a luminometer over several minutes to obtain the initial rates (lumens/sec). The maximum rate of catalysis ($k_{cat}$) was calculated from the Michaelis equation as described in kinetic assays. In cases where slow-onset inhibition was observed, $K_i^*$ was used to define the inhibition. Pre-incubation of inhibitor with saporin-L1, followed by initiation of the reaction with substrate provided a direct measure of $K_i^*$. Values for the inhibition constant ($K_i^*$) were calculated by fitting post slow-onset rates to the equation for competitive inhibition, $v=k_{cat}[S]/[[S]+K_m(1+I/K_i^*)]$, where v is the initial reaction rate, [S] is the substrate concentration, $K_m$ is the Michaelis constant for A-10, and $k_{cat}$ is the initial rate at A-10 saturation. For tight inhibition, when the concentration of inhibitor was ≤5 times the enzyme concentration, a correction was made for free inhibitor concentration. The free inhibitor concentration was determined by the relationship $I=I_t-(1-v_i/v_o)E_t$, where $I_t$ is total inhibitor concentration, $v_i$ and $v_o$ are the inhibited and uninhibited steady-state rates, respectively, and $E_t$ is the total enzyme concentration.

Protein translation assays. Saporin-L1 inhibition of protein translation was determined using a reticulocyte lysate translation system to express luciferase from mRNA as described by the manufacturer. For IC50 determination, 30 µL translation reactions in triplicate with varying concentrations of saporin-L1 were incubated at 37° C. at 1.5 hr. A 10 µL aliquot was sampled and luminescence was measured with a luciferase detection kit (Promega) according to the manufacturer's protocol in a 96-well plate format on a luminometer. Percent translation relative to control was plotted versus the log of saporin-L1 concentration and fit to a dose-response curve for the calculation of IC50.

For EC50 determination, triplicate reactions of 2.1 nM saporin-L1 with increasing inhibitor concentrations were pre-incubated at room temperature for 10 min in 5 µL of buffer (20 mM tris-acetate pH 7.4, 25 mM KCl, 5 mM $MgCl_2$). Translation mix (25 pt) was added (300 µM saporin-L1 final) to the pre-incubated samples and were incubated at 37° C. for 1.5 hours. A 10 µL aliquot was sampled and luminescence was measured with the luciferase detection kit (luminescence) as described above. A control with the maximum inhibitor concentration without saporin-L1 established that the oligonucleotide itself did not affect luciferase expression. Percent translation relative to control (no saporin-L1) was plotted versus the log of inhibitor concentration and was fit to a dose-response curve for the calculation of EC50.

Figure 4:
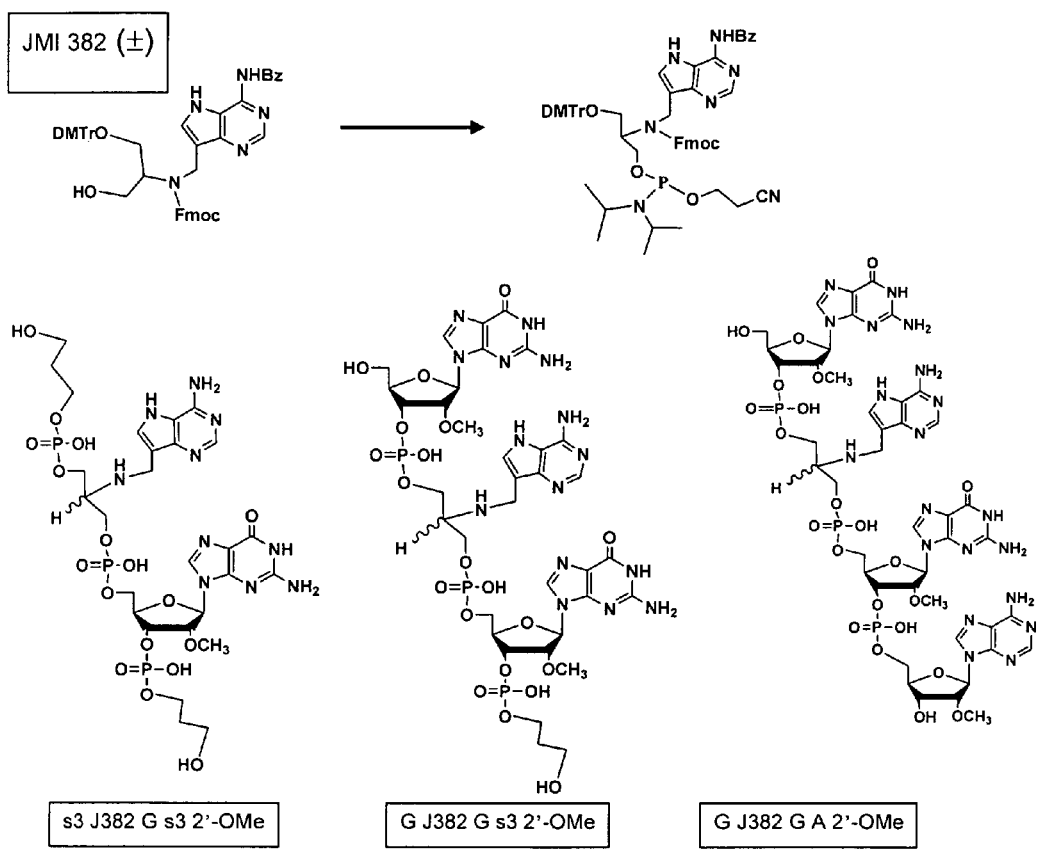
FIG. 4. Saporin inhibitors based on JMI382.

Synthesis of saporin inhibitors based on JMI382. The compound JMI382(±) was converted to phosphoramidite, purified, and incorporated to three different oligonucleotide constructs (FIG. 4). The synthesized inhibitors were purified on HPLC with 5'-Trityl-on mode first, followed by detritylation, then purified again on HPLC. Each inhibitor is a 50:50 mix of two diastereomers. The tri-nucleotide and tetra-nucleotide inhibitors showed two closely placed peaks on HPLC, while the di-nucleotide inhibitor showed only one peak after the trityl group is removed. All products were confirmed by Mass Spec.

Figure 5:
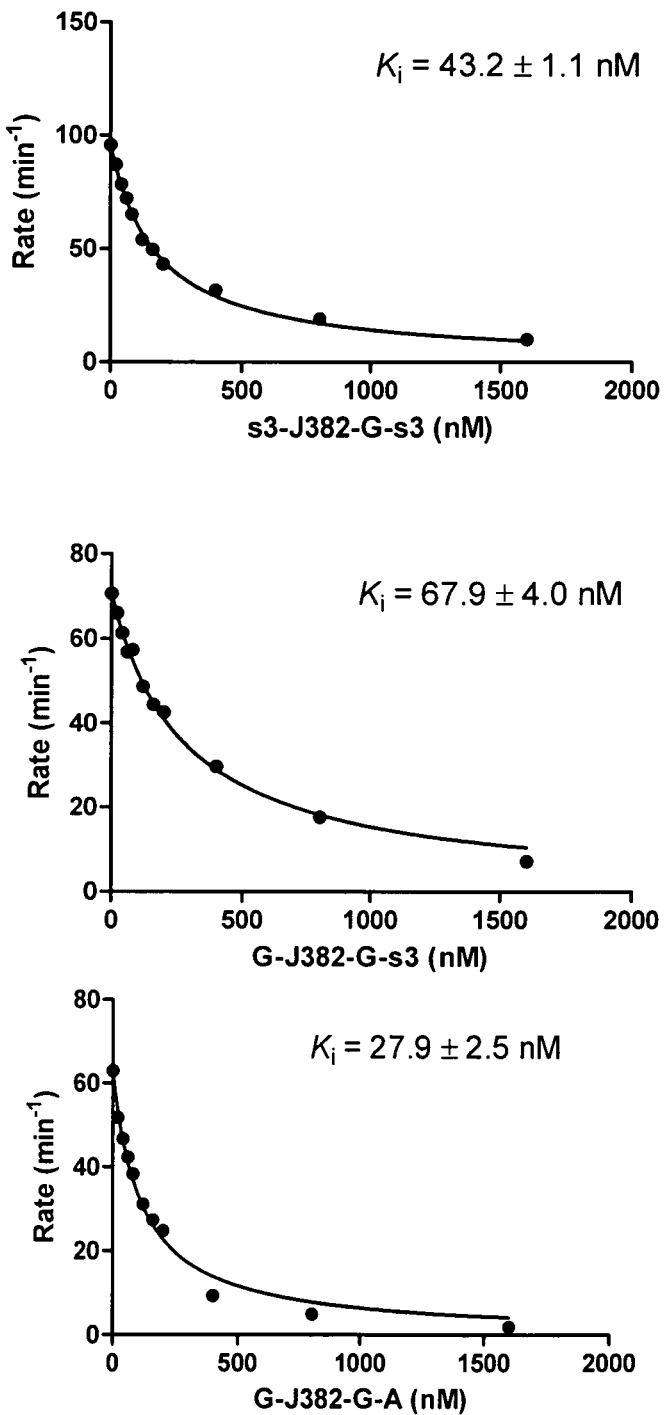
FIG. 5. The inhibition assays of JMI382 based oligonucleotides on Saporin.

These inhibitors were examined on Saporin L1 by continuous luciferase assay. Each inhibitor was assayed by using the diastereomer mix, without further investigation of the more active component. The $K_i$ values are 43.2 nM, 67.9 nM, 27.9 nM respectively for the di-, tri- and tetra-nucleotides (FIG. 5).

Experimental scheme and data for the SerMe building block used for the saporin inhibitors are indicated below.

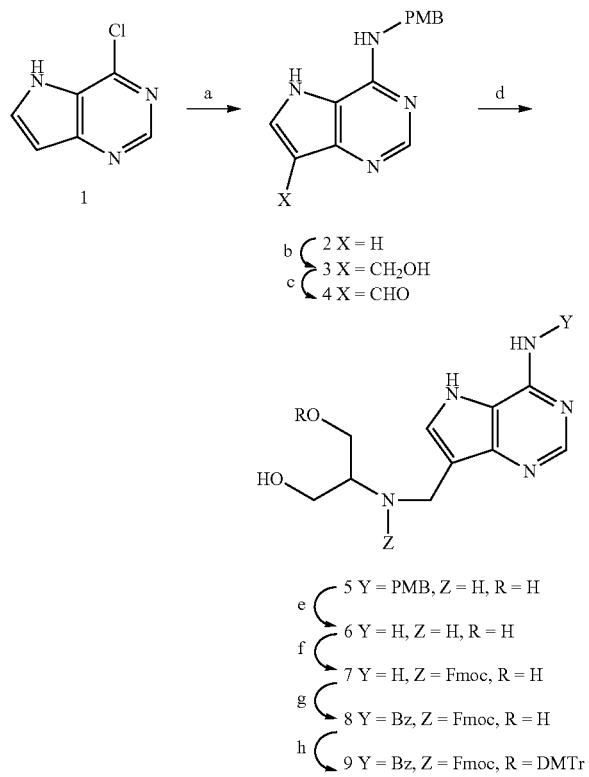

Reagents a) 4-methoxybenzylamine, 100° C., 54%. b) $CH_2O$, $K_2CO_3$, 90° C. c) Dess-Martin periodinane, AcOH, 69% (2 steps). d) serinol, $NaBH_4$. e) TFA, 100° C., 38% (2 steps). f) FmocCl, $NaHCO_3$, 51%. g) TMSCl, BzCl, pyridine, then $NH_3$, 67%. h) DMTrCl, pyridine, 50%.

(9H-Fluoren-9-yl)methyl (4-benzamido-5H-pyrrolo[3,2-d]pyrimidin-7-yl)methyl(1-(bis(4-methoxyphenyl)(phenyl) methoxy)-3-hydroxypropan-2-yl)carbamate 9 (JMI382):

N-(4-methoxybenzyl)-5H-pyrrolo[3,2-d]pyrimidin-4-amine 2: Chloropyrimidine 1 (4.2 g, 27.3 mmol), 4-methoxybenzylamine (10.7 mL, 82 mmol) and ethanol (25 mL) were heated at 100° C. for 6 h. The still warm solution was diluted with methanol, stirred with charcoal and filtered through Celite. Addition of water and ammonia to pH9 gave a precipitate that was isolated by filtration and washed with water, methanol and dichloromethane to give the title amine 2 (3.8 g, 14.9 mmol, 54%) as a brown solid. $^1$H NMR (DMSO d-6) δ 10.91 (s, 1H), 8.18 (s, 1H), 7.48 (bs, 1H), 7.33 (m, 3H), 6.92 (m, 2H), 6.37 (m, 1H), 4.65 (m, 2H), 3.74 (s, 3H).

4-(4-Methoxybenzylamino)-5H-pyrrolo[3,2-d]pyrimidine-7-carbaldehyde 4: Pyrimidine amine 2 (3.8 g, 14.9 mmol), potassium carbonate (5.2 g, 37.4 mmol), aqueous formaldehyde (37%, 40 mL, 1.3 mol), dioxane (320 mL) and water (80 mL) were heated together at 90° C. for 40 min. The cooled solution was evaporated onto silica gel and hydroxymethylpyrimidine 5 (3.2 g, 11 mmol) was isolated by elution through a plug of silica gel with dichloromethane-methanolic ammonia (1.4N), (9:1 and 4:1) and precipitation from aqueous methanol. A portion (1.4 g, 4.9 mmol) of this material was dissolved in acetic acid (50 mL) and stirred with Dess-Martin periodinane (2.5 g, 5.9 mmol) for 1 h. The solution was concentrated to a small volume and poured into a mixture of sodium bicarbonate (10%, aqueous, 50 mL) and sodium thiosulphate (5%, aqueous, 50 mL). Filtration gave the title aldehyde 4 (1.5 g, 4.52 mmol, 69%) contaminated with 15 mol % of iodobenzoic acid salts. This material was used in the next step; a small sample was further purified by chromatography on silica eluted with dichloromethane-methanol (9:1). $^1$H NMR (DMSO d-6) δ 11.9 (bs, 1H), 10.11 (s, 1H), 8.37 (s, 1H), 8.21 (s, 1H), 7.62 (bs, 1H), 7.33 (m, 2H), 6.92 (m, 2H), 6.37 (m, 1H), 4.66 (m, 2H), 3.74 (s, 3H). $^{13}$C NMR (DMSO d-6) 184.6, 158.4, 152.3, 149.6, 144.7, 134.1, 130.7, 129.0, 116.7, 114.6, 113.9, 55.2, 42.9. ESI-MS+, found 283.1198, calc. for $C_{15}H_{15}N_4O_2$ [M+H]+ 283.1195.

2-((4-Amino-5H-pyrrolo[3,2-d]pyrimidin-7-yl)methylamino)propane-1,3-diol 6. Aldehyde 5 (1.5 g, 85%, 4.2 mmol) was suspended in methanol (100 mL) containing serinol (0.49 g, 5.4 mmol) and stirred at room temperature overnight. Sodium borohydride (170 mg, 4.5 mmol) was added to the resulting solution and stirring was continued for a further 30 min. The solution was evaporated to dryness. Chromatography of the residue on silica gel eluted with dichloromethane-methanolic ammonia (1.4 M) (1:1) gave serinol adduct 7 (0.9 g, 56%). This compound was dissolved in trifluoroacetic acid (12 mL) and heated in a microwave oven to 100° C. for 8 min. After cooling the solvents were removed under reduced pressure. Purification of the residue on a column of silica gel eluted with dichloromethane-methanolic ammonia (3.5 M), 2:1 and 1:1, gave the title compound as a pale yellow glassy solid (0.38 g, 1.6 mmol, 38%). $^1$H NMR ($D_2O$) δ 7.88 (s, 1H), 7.24 (s, 1H), 3.76 (s, 2H), 3.62 (dd, J=5.5, 11.6 Hz, 2H), 3.54 (dd, J=5.6, 11.6, 2H), 2.77 (m, 1H). $^{13}$C NMR ($D_2O$) 150.2, 149.6, 144.6, 128.6, 113.6, 112.0, 60.7, 58.9, 39.6. ESI-MS+, found 238.1307, calc. for $C_{10}H_{16}N_5O_2$ [M+H]+ 238.1304.

(9H-Fluoren-9-yl)methyl (4-amino-5H-pyrrolo[3,2-d]pyrimidin-7-yl)methyl(1,3-dihydroxypropan-2-yl)carbamate 7: Amine 6 (330 mg, 1.4 mmol) was suspended in methanol (35 mL) and 10% aqueous $NaHCO_3$ (3.5 mL). Fmoc chloride (432 mg, 1.7 mmol) was added and the solution stirred for 15 min. The suspension was concentrated under reduced pressure. Chromatography of the residue on a column of silica gel eluted with 7.5-20% methanol in dichloromethane gave the title compound 7 (150 mg, 0.33 mmol, 48% allowing for recovered starting material). Subsequent elution with 50% methanolic ammonia (3.5M) in dichloromethane returned the starting amine 6 (170 mg, 51%). 7, colourless amorphous solid, ESI-MS+, found 460.1975, calc. for $C_{25}H_{26}N_5O_5$ [M+H]+ 460.1985.

(9H-Fluoren-9-yl)methyl (4-benzamido-5H-pyrrolo[3,2-d]pyrimidin-7-yl)methyl(1,3-dihydroxypropan-2-yl)carbamate 8: Chlorotrimethylsilane (810 μL, 6.3 mmol) was added to a solution of 7 (194 mg, 0.42 mmol) in dry pyridine. After 30 min benzoyl chloride (172 μL, 1.48 mmol) was added and the solution was stirred overnight. The reaction was quenched by the addition of water and concentrated to dryness. The residue was taken up in dichloromethane (10 mL), washed with water, concentrated, stirred for 5 min in methanolic ammonia (7N) and concentrated again. Chromatography of the residue on silica gel eluted with 4% methanol in dichloromethane gave the title compound as a colourless, amorphous solid (160 mg, 2.84 mmol, 67%). ESI-MS+, found 564.2245, calc. for $C_{32}H_{30}N_5O_5$ [M+H]+ 564.2245.

(9H-Fluoren-9-yl)methyl (4-benzamido-5H-pyrrolo[3,2-d]pyrimidin-7-yl)methyl(1-(bis(4-methoxyphenyl)(phenyl)

methoxy)-3-hydroxypropan-2-yl)carbamate 9 (JMI382): Compound 8 (220 mg, 0.39 mmol) was evaporated from pyridine and then redissolved in the same solvent (12 mL). Dimethoxytrityl chloride (160 mg, 0.47 mmol) was added and the solution was stirred for 48 h. Solvent was removed under reduced pressure and the residue partitioned between dichloromethane and NaHCO$_3$ solution (10% aqueous). Evaporation of the solvent and chromatography of the residue on a column of silica gel eluted with ethyl acetate gave the title compound as an amorphous solid (170 mg, 0.20 mmol, 50.3%). ESI-MS+, found 866.3545, calc. for $C_{53}H_{48}N_5O_7$ [M+H]$^+$ 866.3554. HPLC (Waters XBridge-C8, 60-100% CH$_3$CN in water) R$_T$ 5.1 min, 98.4%.

Results and Discussion

Saporin-L1 Catalysis. Initial rate kinetics were measured by coupling the adenine product to a luciferase-luciferin coupled assay with quantitation via luminescence (13). Saporin-L1 catalyzed deadenylation of A-10 gave a hyperbolic saturation curve with a $k_{cat}$=440±16 min$^{-1}$ and $K_m$=95±7 µM at pH 7.7 (Table 2). MALDI-TOF analysis of the saporin-L1 reaction product showed that both adenosines in the GAGA tetraloop of A-10 were depurinated during prolonged incubations. Cyclic oxime RNA GAGA, a circular oligonucleotide substrate, was also depurinated by saporin-L1 with kinetics comparable to A-10 RNA with a $k_{cat}$=301±27 min$^{-1}$ and $K_m$=82±15 µM (Table 2). The synthetic linker in circular oxime GAGA substrates folds the tetraloop for RIP recognition and is proposed to mimic the structure of stem-loop oligonucleotides (FIG. 1) (16). Linear GAGA was also investigated as a saporin-L1 substrate and gave a $k_{cat}$=293±29 min$^{-1}$ and $K_m$=266±39 µM (Table 2). The $K_m$ for linear GAGA is ~3-fold higher than for A-10 or cyclic oxime RNA substrate while the catalytic turnover rate ($k_{cat}$) is comparable. Linear GAGA is less structured in solution than stem-loop or cyclic oligonucleotides and requires higher concentrations for equivalent catalytic rates. Previous kinetic constants for saporin-L1 catalysis have been reported for poly(A) RNA with a $k_{cat}$=61±1 min$^{-1}$ and $K_m$=639±32 µM at pH 7.8 (Table 2) (5). A-10 RNA depurination by saporin-L1 is 10-fold faster ($k_{cat}$) and 4.5-fold tighter ($K_m$) than poly(A) RNA under comparable conditions, to give a 45-fold increased catalytic efficiency ($k_{cat}/K_m$).

TABLE 2

Kinetic Parameters for Saporin-L1

| Substrate | $k_{cat}$ (min$^{-1}$) | $K_m$ (µM) | $k_{cat}/K_m$ (M$^{-1}$s$^{-1}$) |
|---|---|---|---|
| A-10 RNA | 440 ± 16 | 95 ± 7 | 7.7 × 10$^4$ |
| cyclic oxime GAGA | 301 ± 27 | 82 ± 15 | 6.1 × 10$^4$ |
| linear GAGA | 293 ± 29 | 266 ± 39 | 1.8 × 10$^4$ |
| poly(A)* | 61 ± 1 | 639 ± 32 | 1.6 × 10$^3$ |
| A-10 RNA (saporin-S6) | 0.35 ± 0.04 | 360 ± 60 | 16 |

*kinetic constants for poly(A) were previously reported in 20 mM Tris/HCl, pH 7.8, 100 mM NH$_4$Cl, 10 mM magnesium acetate (5).

Saporin-S6 catalysis. A-10 catalysis by saporin-S6, an RIP from *Saponaria officinalis* seeds, was also measured. Saporin-S6 was a commercial preparation and was further purified to remove contaminating saporin-L1. Saporin-S6 and saporin-L1 co-eluted on carboxymethyl resin but were separated by heparin chromatography. Saporin-S6 initial rate catalysis of A-10 RNA as substrate gave a $k_{at}$ of 0.35±0.04 min$^{-1}$ and $K_m$ of 360±60 µM at pH 7.7 (Table 2). Saporin-L1 catalyzes ($k_{cat}$) A-10 RNA approximately 1,500 times faster and has a 4-fold lower $K_m$ than saporin-S6. Thus, saporin-L1 is 4.800-fold more efficient ($k_{cat}/K_m$) at catalyzing A-10 RNA depurination than saporin-S6 (Table 2). Ricin A-chain is incapable of a single turnover of A-10 above pH 6.5 but at pH 4.0 gives a $k_{cat}$ of ~4 min$^{-1}$ on this substrate (18). Saporin-S6 was previously reported to catalyze the depurination of a 35-mer synthetic SRL mimic with GAGA tetraloop at pH 7.6 with a $k_{cat}$ of 0.4 min$^{-1}$ and $K_m$ of 9 µM, while RIPs trichosanthin, gelonin, cinnamomin A-chain, and ricin A-chain had no detectable activity at physiological pH values (19).

Action of Saporin-L1 on 80S Ribosomes. Saporin-L1 action on 80S rabbit reticulocyte ribosomes (40 nM) showed multiple adenines released with a rate of 50 min$^{-1}$ which is 250-fold faster than adenine release from A-10 RNA at an equivalent concentration. A continuous, linear rate was observed for the formation of adenine from 80S rabbit ribosomes extending well past one adenine/ribosome. Thus, saporin-L1 lacks sarcin-ricin loop specificity as the primary ribosomal depurination target. Previous reports indicate that saporin-L1 depurinates up to 36 adenines/mol from 80S rat ribosomes while saporin-S6 releases 1 to 2.5 adenine/mol (20). Moreover, saporin-L1 was reported to release ~6 adenines from 80S rat ribosome before 50% inhibition of protein synthesis was observed in in vitro translation assays with a poly(U) transcript (5). Thus, adenines other than those at the sarcin-ricin loop are removed preferentially. Most other ribosome inactivating proteins are highly specific in releasing one mole of adenine per mole ribosome from the eukaryotic sarcin-ricin loop (1). Thus, both ricin A-chain and saporin-S6 release only 1 mole adenine per mole 80S rabbit ribosome in the present assay conditions. Ribosomal proteins surrounding the sarcin-ricin loop are known to influence the ribotoxic mechanism of RIP substrate recognition (21, 22).

Figures 2A, 2B:
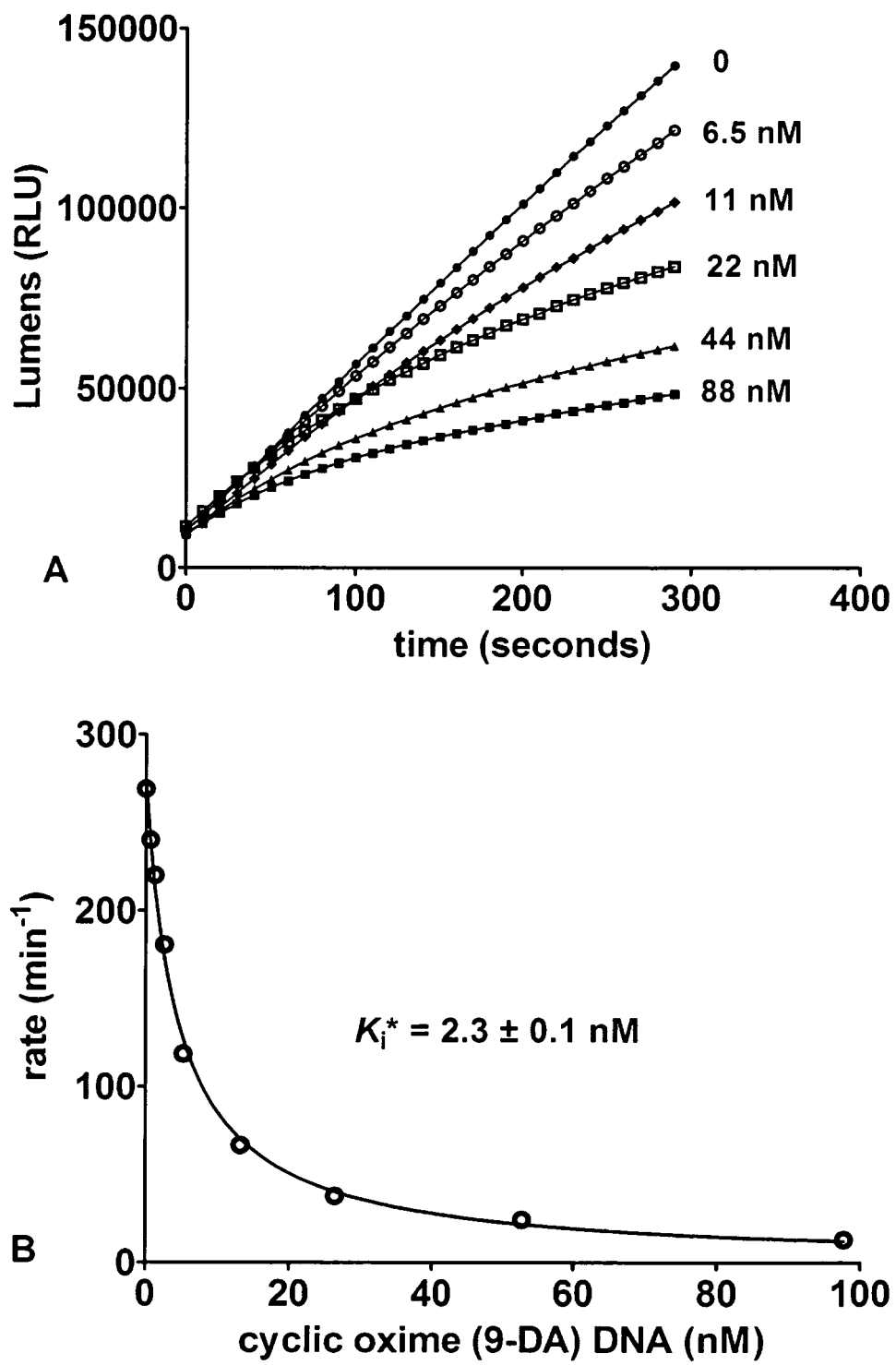
FIG. 2A-2B. Slow-onset inhibition of saporin-L1 by transition state mimics. A) Plot of lumens (RLU) versus time for saporin-L1 catalysis of A-10 with increasing inhibitor [A14 (9-DA) 2'-OMe] concentrations. B) Competitive inhibition curve fit of rate versus increasing concentrations of tetramer cyclic oxime G(9-DA)GA DNA inhibitor. Kinetics were measured after a 10 minute enzyme-inhibitor pre-incubation equilibration to achieve slow onset binding ($K_i^*$).
Figures 3A, 3B:
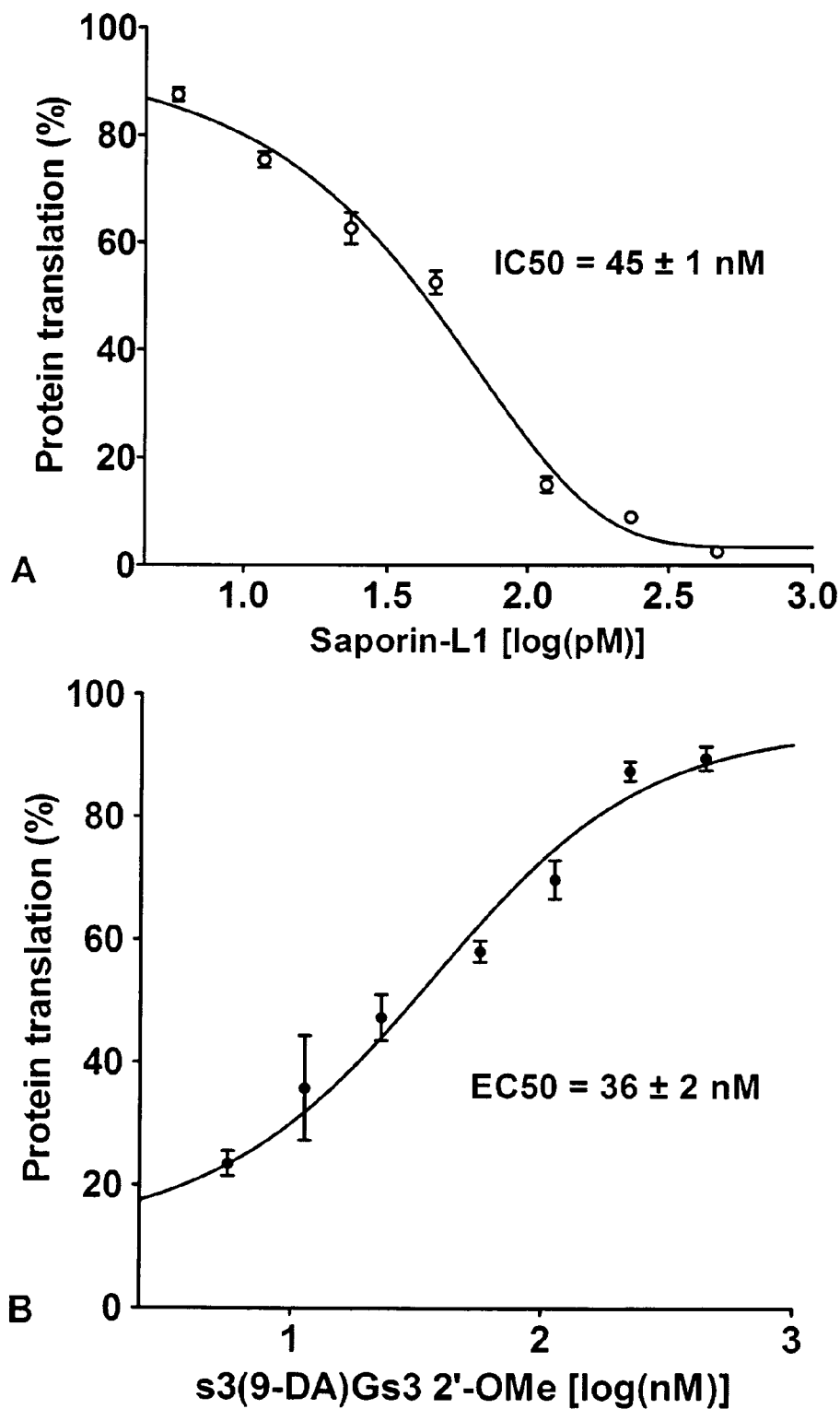
FIG. 3A-3D. Inhibition of translation by saporin-L1 and protection by saporin-L-1 inhibitors. A) Saporin-L1 inhibition of protein translation (% relative to control) in rabbit reticulocyte lysate assays. The mean and SEM error of triplicate data points were fit to a dose-response curve. B) Protein translation rescue from 300 µM of saporin-L1 (% relative to no saporin-L1) with increasing concentrations [log(nM)] of dimer s3 (9-DA)Gs3 inhibitor in a ribosome reticulocyte lysate assay. The mean and SEM error of triplicate data points were fit to a dose-response curve. C) Saporin-L1 (300 µM) rate of adenine release from 40 nM 80S ribosome versus concentrations of s3(9-DA)Gs3 inhibitor. D) Plot of FIG. 3C as a dose-response curve fit for percentage of 80S catalysis [% relative to no s3(9-DA)Gs3)] versus increasing concentrations [log(nM)] of dimer s3(9-DA)Gs3 inhibitor.
Figures 3C, 3D:
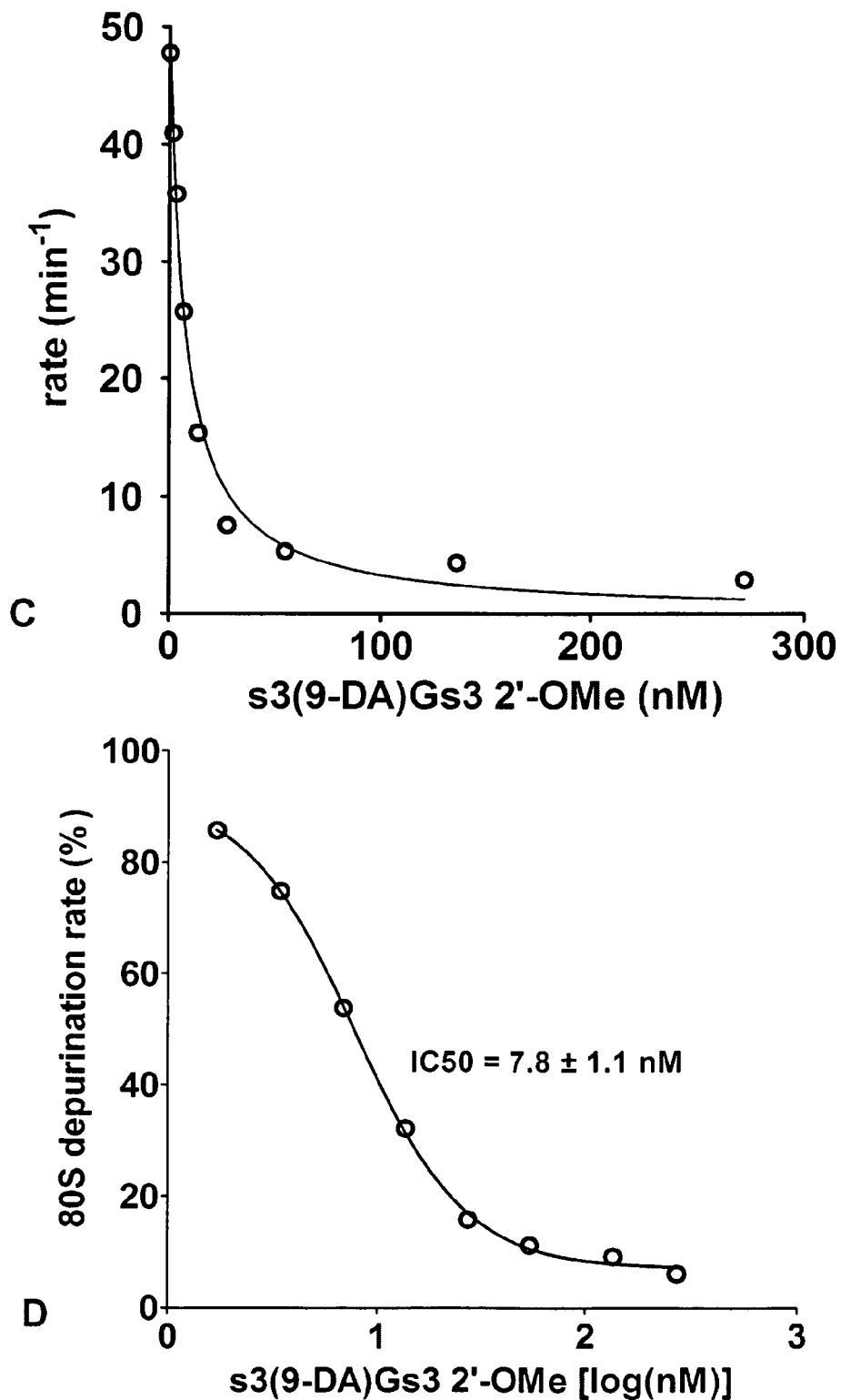

Saporin-L1 Inhibitors. DADMeA (9-DA in Figures) is a non-hydrolysable methylene bridged 9-deazaadenine 1-aza sugar with features of the transition state for depurination of A-10 constructs by ricin A-chain. The replacement of N for C at C1' of the ribosyl group mimics the carbocation of the dissociated transition state (8, 10). Replacing adenine with 9-deazaadenine caused an elevated pK$_a$ at N7, another feature of the transition state. The methylene linker between the 9-deazaadenine and the hydroxypyrrolidine places the base analogue and ribocation at approximately the same distance as found at the transition state. The omission of the 2'-hydroxyl found in RNA is required for the chemical stability of 9-DA. Replacing the scissile adenosine with 9-DA within the 14-mer stem-loop [A-14 (9-DA) RNA] competitively inhibited saporin-L1 with A-10 RNA as substrate with a K$_i$* of 3.7±0.7 nM at pH 7.7 (Table 3). The slow onset inhibition (K$_i$*) observed for saporin-L1 binding of inhibitors such as A-14 (9-DA) RNA was common to all inhibitor constructs listed in Table 2 excluding s3(9-DA)s3 and 9-DA (FIG. 2). Inhibitor A-14 (9-DA) DNA oligonucleotide inhibited saporin-L1 with a K$_i$* of 3.1±0.5 nM, similar to A-14 (9-DA) RNA (Table 3). 2'-OMe A-14 (9-DA), a nuclease stable 14-mer oligonucleotide is also similar to the RNA/DNA versions with a K$_i$* value of 5.6±0.8 nM (Table 3). Thus, high binding affinity is observed between A-14 (9-DA) constructs in RNA, DNA, and 2'-OMe structural motifs. A 10-mer inhibitor A-10 (9-DA) 2'OMe had a K$_i$* of of 4.2±1.3 nM, similar to 2'-OMe A-14 (9-DA) (Table 3). This observation is reminiscent of previous reports with ricin A-chain in showing similar K$_m$ values for small constructs of RNA, DNA, and 2'-OMe modified substrates (23). Limited quantitative kinetic and substrate specificity data are available for other RIPs.

TABLE 3

Inhibition Constants for Saporin-L1 inhibitors[A]

| Inhibitor | $K_i^*$ (nM) |
| --- | --- |
| A-14 (9-DA) 2'-OMe | 5.6 ± 0.8 |
| A-14 (9-DA) RNA | 3.7 ± 0.7 |
| A-14 (9-DA) DNA | 3.1 ± 0.5 |
| A-10 (9-DA) 2'-OMe | 4.2 ± 1.3 |
| cyclic oxime (9-DA) 2'-OMe | 3.9 ± 0.5 |
| cyclic oxime (9-DA) DNA | 2.3 ± 0.1 |
| G(9-DA)GA 2'-OMe | 8.7 ± 2.3 |
| G(9-DA)Gs3 2'-OMe | 7.5 ± 1.6 |
| s3(9-DA)Gs3 2'-OMe | 6.4 ± 1.7 |
| s3(9-DA)s3 | 690 ± 100[B] |
| 9-DA | >0.5 × 10[6B] |

[A]See FIG. 1 for structures of inhibitors.
[B]Values are $K_i$ with no slow onset observed.

Circular Inhibitors. Cyclic DNA and cyclic 2'-OMe modified G(9-DA)GA oligonucleotides inhibited saporin-L1 with $K_i^*$ values of 2.3±0.1 nM and 3.9±0.5 nM respectively (Table 3, FIG. 2B). Thus, 9-DA cyclic tetramers inhibit saporin-L1~1.4 fold tighter than the larger A-14 stem-loop counterparts. This similarity in $K_i^*$ supports a primary role for the stem in sarcin-ricin stem-loop mimics to fold the tetraloop for RIP recognition (16). Circular oxime (9-DA) DNA binds saporin-L1 ~40,000-fold tighter than A-10 RNA or cyclic oxime RNA substrate, a gain of ~6 kcal/mole in binding energy.

Linear Inhibitors. Monomer, linear dimer, trimer and tetramer inhibitor scaffolds containing 9-DA in the RTA-scissile adenosine position were also investigated (FIG. 1). Linear tetramer G(9-DA)GA 2'-OMe bound saporin-L1 only ~2-fold less tightly than its cyclic oxime counterpart and gave a $K_i$* of 8.7±2.3 nM (Table 3). Linear trimer [G(9-DA)Gs3] and dimer [s3(9-DA)Gs3] 2'-OMe inhibitors bound comparably with $K_i$* values of 7.5±1.6 nM and 6.4±1.7 nM respectively (Table 2, FIG. 1). The linear dimer s3(9-DA)Gs3 phosphodiester also binds with affinity similar to stem-loop and cyclic oxime 2'-OMe inhibitors (Table 3). A monomer phosphodiester (s3(9-DA)s3) inhibited saporin-L1 with a $K_i$* value of 690±100 nM while 9-DA alone was not an inhibitor (Table 3). Dimer (s3(9-DA)Gs3) is the tightest linear inhibitor to saporin-L1, binding 15.000-fold tighter than A-10 RNA, a gain of ~5.6 kcal/mole in binding energy. Removal of the 3'-Gs3 moiety of dimer inhibitor to give monomer (s3(9-DA) s3) reduced binding affinity to saporin-L1 10-fold and therefore binding energy by ~2-fold (Table 3). Thus, the 3'-Gs3 moiety of dimer s3(9-DA)Gs3 contributes half the binding energy for inhibitor association with saporin-L1. NMR structural determinations of GAGA tetraloops and the reported crystal structure of a 29-mer RNA SRL mimic show the $G_1A_2G_3A_4$ tretraloop conformation with $A_2$ and $G_3$ available for direct hydrogen bonding while the $G_1$ and $A_4$ form a sheared base pair (24-25). Surprisingly, none of the inhibitors for saporin-L1 (Table 3) were effective against saporin-S6 at concentrations up to 10 μM. Saporin-S6 also catalyzes A-10 de-adenylation but at a much slower rate and higher $K_m$ (Table 2).

Saporin-L1 Translation Inhibition. Saporin-L1 inhibited the translation of luciferase mRNA by rabbit reticulocyte lysate in a cell-free translation assay with an IC50 of 45 pM (FIG. 3A). Previous reports of saporin-L1 inhibition (IC50) in ribosome translational assays are comparable and vary from 250 pM to 11 nM with poly (U) mRNA for polyphenylalanine expression (5, 6, 7). Saporin-L1 has been reported to release more than 6 moles of adenine per ribosome to cause the arrest of translation (5). Although the sarcin-ricin loop is not the first adenylate targeted by saporin-L1 in the 80S ribosome, the robust depurination activity is highly toxic to ribosomes and protein translation. Ricin A-chain and saporin-S6 specifically depurinate the sarcin-ricin loop and have IC50 values of 30 pM and 8 pM respectively in rabbit reticulocyte lysate translation assays, similar to that of 45 pM for saporin-L1 (FIG. 3A) (26).

Saporin-L1 Inhibitor Implications for Toxin Immunotherapy. Saporin-L1 immunotoxin conjugates have been shown to be equally cytotoxic to cells as saporin-S6 conjugates (27). The catalytic A-chains of saporin-S6 and ricin have been investigated as anticancer agents in phase I/II clinical trials using chimeric immunotoxin conjugates in the treatment of lymphomas (11, 28, 29, 30). Therapeutic uses of immunotoxins have been limited by the vascular leak syndrome, a side effect resulting from inappropriate toxin targeting to the capillary bed of endothelial cells, causing edema and multi-organ failure (12, 31, 32, 33). Thus, cancer therapies that employ RIP-linked immunotoxins remain a challenge. Inhibitors to RIPs could provide a way to rescue normal cells following treatment of a targeted tissue with immunotoxins.

Saporin-L1 translation inhibition rescue by TS inhibitor. Protein translation, its inhibition by saporin-L1, and its rescue by inhibitors were studied in rabbit reticulocyte preparations. The minimal saporin-L1 inhibitor dinucleotide s3(9-DA)Gs3 2'-OMe was used (FIG. 1). Saporin-L1 toxicity to cell-free translation caused ~90% inhibition at 300 μM saporin-L1 and was rescued by increasing concentrations of s3(9-DA)Gs3 with an EC50 of 36±2 nM (FIG. 3B). The EC50 to $K_i$* ratio for s3(9-DA)Gs3 comparing translation assays and inhibition kinetics was ~6, supporting strong saporin-L1 inhibition in complex assays at physiological pH (FIG. 3B, Table 3). Dinucleotide s3(9-DA)Gs3 also inhibits saporin-L1 adenine release from purified 80S rabbit ribosomes and gave an IC50 of 7.8±1.1 nM (FIG. 2C, 2D). The calculation of a $K_m$ value for 80S rabbit ribosomes was limited by practical concentrations of ribosomes from reticulocyte lysate and therefore precluded direct $K_i$* calculation. However, the 1050 value for s3(9-DA)Gs3 was comparable to the $K_i$* measured for s3(9-DA)Gs3 in A-10 competition assays (FIG. 2D, Table 3). Thus, transition state (TS) inhibitors of saporin-L1 are equally effective in preventing ribosome depurination and depurination of small nucleic acid substrates.

Saporin-L1 is highly active on mammalian ribosomes and potently inhibited by the transition state mimic DADMeA (9-DA) when incorporated into the depurination site of stem-loop, circular and linear nucleic acid scaffolds appropriate for RIP recognition. This activity occurs at physiological conditions. The oligonucleotide context is essential as 9-DA alone is a poor inhibitor. Small oligonucleotide inhibitors featuring DADMeA bind up to 40,000 fold tighter than small stem-loop RNA substrates. Nine inhibitors exhibited slow onset binding to saporin-L1 with dissociation constants from 8.7 to 2.3 nM. Inhibitors constructed on RNA, 2'-OMe, and DNA scaffolds supported 9-DA binding with only small scaffold effects. Covalently closed circular inhibitors constructed on DNA or 2'-OMe RNA scaffolds were also excellent inhibitors. Dinucleotide s3(9-DA)Gs3 was the smallest tight binding inhibitor of saporin-L1. In ribosome translation rescue assays, s3(9-DA)Gs3 restored protein synthesis by inhibiting saporin-L1 depurination activities. Direct competition assays between 80S rabbit ribosomes and s3(9-DA)Gs3 established saporin-L1 inhibition with a dissociation constant of 7.8 nM.

Transition state inhibitor efficacy for RIP activity at physiologic pH has been previously limited by the pH 4.0 activity used for development of ricin A-chain transition state analogues. Ricin A-chain and other type I and II RIPs have a low pH catalytic optimum on nucleic acid substrates such as stem-loop RNA, poly(A) and/or hsDNA, while the natural ribosome substrate is depurinated optimally at physiologic pH (6, 18, 34). Saporin-S6 has a substrate specificity distinct from saporin-L1 and was not inhibited by saporin-L1 transition state mimics at neutral pH. Saporin-L1 rapidly catalyzes depurination of stem-loop, circular, and linear truncated mimics of the sarcin-ricin loop at neutral pH, a unique feature in the RIP family of N-glycohydrolases (Table 2) (35). Although saporin-L1 is reported to catalyze adenine release from poly(A), hsDNA, tRNA, *E. coli* rRNA, and globin mRNA at pH 7.8 (5, 6), the 80S ribosome is a preferred substrate.

Tight-binding inhibitors of saporin-L1 that prevent ribosome damage at physiological pH provide a breakthrough in developing immunotoxin cancer therapy. It should be possible to use saporin-L1 conjugates to target cancer cells. Following tumor lysis, rescue of the organism from vascular leak syndrome might be affected with the small, stable, and tight-binding inhibitors of saporin-L1 characterized here.

REFERENCES

1. Endo, Y., Mitsui, K., Motizuki, M., and Tsurugi, K. (1987) The mechanism of action of ricin and related toxic lectins on eukaryotic ribosomes. The site and the characteristics of the modification in 28 S ribosomal RNA caused by the toxins *J. Biol. Chem.* 262, 5908-5912.
2. Polito, L., Bortolotti, M., Farini, V., Battelli, M. G., Barbieri, L., and Bolognesi, A. (2009) Saporin induces multiple death pathways in lymphoma cells with different intensity and timing as compared to ricin. *Inter. Journ. of Biochem. and Cell Biol.* 41, 1055-1061.
3. Barbieri, L., Valbonesi, P., Bonora, E., Gorini, P., Bolognesi, A., and Stirpe, F. (1997) Polynucleotide:adenosine glycosidase activity of ribosome-inactivating proteins: effect on DNA, RNA and poly(A). *Nucleic Acids Res.* 25, 518-522.
4. Barbieri, L., Valbonesi, P., Govoni, M., Pession, A., and Stirpe, F. (2000) Polynucleotide:adenosine glycosidase activity of saporin-L1: effects on various forms of mammalian DNA. *Biochimica et Biophysica Acta* 1480, 258-266.
5. Barbieri, L., Valbonesi, P., Gorini, P., Pession, A., and Stirpe, F. (1996) Polynucleotide: adenosine glycosidase activity of saporin-L1: effect on DNA, RNA and poly (A). *Biochem. J.* 319, 507-513.
6. Barbieri, L., M. Ciani, T. Girbes, W. Liu, E. J. M. Van-Damme, W. J. Peumans, and F. Stirpe (2004) Enzymatic activity of toxic and non-toxic type 2 ribosome-inactivating proteins. *FEBS Letters* 563, 219-222.
7. Ferreras, J. M., Barbieri, L, Girbes, T., Battelli, M. G, Rojo, M. A., Arias, F. J, Rocher, M. A., Soriano, F., Mendéz, E., and Stirpe, F. (1993) Distribution and properties of major ribosome-inactivating proteins (28 S rRNA N-glycosidases) of the plant *Saponaria officinalis* L (Caryophyllaceae). *Biochimica et Biophysica Acta* 1216, 31-42.
8. Roday, S., Amukele, T., Evans, G. B., Tyler, P. C., Furneaux, R. H., and Schramm, V. L. (2004) Inhibition of Ricin A-Chain with Pyrrolidine Mimics of the Oxacarbenium Ion Transition State. *Biochemistry* 43, 4923-33.
9. Chen, X.-Y., Berti, P. J., and Schramm, V. L. (2000) Transition-State Analysis for Depurination of DNA by Ricin A-Chain *J. Am. Chem. Soc.* 122, 6527-6534.
10. Chen, X.-Y., Berti, P. J., and Schramm, V. L. (2000) Ricin A-Chain: Kinetic Isotope Effects and Transition State Structure with Stem-Loop RNA. *J. Am. Chem. Soc.* 122, 1609-1617.
11. Schnell, R., Borchmann, P., Staak, J. O., Schindler, J., Ghetie, V., Vitetta, E. S., and Engert, A. (2003) Clinical evaluation of ricin A-chain immunotoxins in patients with Hodgkin's lymphoma. *Annals of Oncology* 14, 729-736.
12. Baluna, R., and Vitetta, E. S. (1997) Vascular leak syndrome: A side effect of immunotherapy. *Immunopharmacology* 37, 117-132.
13. Sturm, M. B., and Schramm, V. L. (2009) Detecting ricin: sensitive luminescent assay for ricin A-chain ribosome depurination kinetics. *Anal. Chem.* 81, 2847-2853.
14. Singh, V., Evans, G. B., Lenz, D. H., Mason, J. M., Clinch, K., Mee, S., Painter, G. F., Tyler, P. C., Furneaux, R. H., Lee, J. E., Howell, P. L., and Schramm, V. L. (2005) Femtomolar transition state analogue inhibitors of 5'-methylthioadenosine/S-adenosylhomocysteine nucleosidase from *Escherichia coli. J. Biol. Chem.* 280, 18265-18273.
15. Angelis, F. D., Tullio, A. D., Spano, L. and Tucci, A. (2001) Mass spectrometric study of different isoforms of the plant toxin saporin. *Journal of Mass Spectrometry* 36, 1237-1239.
16. Sturm, M. B., Roday, S, and Schramm, V. L. (2007) Circular DNA and DNA/RNA Hybrid Molecules as Scaffolds for Ricin Inhibitor Design. *J. Am. Chem. Soc.* 129, 5544-5550.
17. Wincott, F., DiRenzo, A., Shaffer, C., Grimm, S., Tracz, D., Workman, C., Sweedler, D., Gonzalez, C., Scaringe, S., and Usman, N. (1995) Synthesis, deprotection, analysis and purification of RNA and ribozymes. *Nucleic Acids Res.* 23, 2677-84.
18. Chen, X. Y., Link, T. M. and Schramm, V. L. (1998) Ricin A-Chain: Kinetics, Mechanism, and RNA Stem-Loop Inhibitors. *Biochemistry* 37, 11605-11613.
19. Tang, S., Hu, R., Liu, W., and Ruan, K. (2000) Non-Specific Depurination Activity of Saporin-S6, a Ribosome-Inactivating Protein, under Acidic Conditions. *Biol. Chem.* 381, 769-772.
20. Barbieri, L., Ferreras, J. M., Barraco, A., Ricci, P. and Stirpe, F. (1992) Some ribosome-inactivating proteins depurinate ribosomal RNA at multiple sites. *Biochem. J.* 286, 1-4.
21. Vater, C. A., Bartle, L. M., Leszyk, J. D., Lambert, J. M., and Goldmacher, V. S. (1995) Ricin A chain can be chemically cross-linked to the mammalian ribosomal proteins L9 and L10 e. *J. Biol. Chem.* 270, 12933-12940.
22. Chan, D. S., Chu, L. O., Lee, K. M., Too, P. H., Ma, K. W., Sze, K. H., Zhu, G., Shaw, P. C. and Wong, K. B. (2007) Interaction between trichosanthin, a ribosome-inactivating protein, and the ribosomal stalk protein P2 by chemical shift perturbation and mutagenesis analyses. *Nucleic Acids Res.* 35, 1660-1672.
23. Amukele, T. K. and Schramm, V. L. (2004) Ricin A-chain substrate specificity in RNA, DNA, and hybrid stem-loop structures. *Biochemistry* 43, 4913-4922.
24. Correll, C. C., Munishkin, A., Chan, Y. L., Ren, Z., Wool, I. G. and Steitz, T. A. (1998) Crystal structure of the ribosomal RNA domain essential for binding elongation factors. *Proc. Natl. Acad. Sci. USA* 95, 13436-13441.
25. Jucker, F. M, Heus, H. A., Yip, P. F., Moors, E. H., and Pardi, A. (1996) A network of heterogeneous hydrogen bonds in GNRA tetraloops. *J. Mol. Biol.* 264, 968-980.

26. Hale, M. (2001) Microtiter-Based Assay for Evaluating the Biological Activity of Ribosome-Inactivating Proteins. *Pharmacol Toxicol.* 88, 255-260.
27. Barbieri, L., Bolognesi, A., Valbonesi, P., Polito, L., Olivieri, F., and Stirpe, F. (2000) Polynucleotide: Adenosine Glycosidase Activity of Immunotoxins Containing Ribosome-Inactivating Proteins. *Journal of Drug Targeting* 8, 281-288.
28. Blakey, D. C., Skilleter, D. N., Price, R. J., Watson, G. J., Hart, L. I., Newell, D. R. and Thorpe, P. E. (1988) Comparison of the Pharmacokinetics and Hepatotoxic Effects of Saporin and Ricin A-Chain Immunotoxins on Murine Liver Parenchymal Cells. *Cancer Research* 48, 7072-7078.
29. Falini, B., Bolognesi, A., Flenghi, L., Tazzari, P., Broe, M., Stein, H., Dtirkop, H., Aversa, F., Corneli, R., Pizzolo, G. Barbabietola, G., Sabattini, E., Pileri, S., Martelli, M., and Stirpe, F. (1992) Response of refractory Hodgkin's disease to monoclonal anti-CD30 immunotoxin. *Lancet* 339, 1195-1196.
30. Polito, L., Bolognesi, A., Tazzari, P. L., Farini, V., Lubelli, C., Zinzani, P. L., Ricci, F., and Stirpe, F. (2004) The conjugate Rituximab/saporin-S6 completely inhibits clonogenic growth of CD20-expressing cells and produces a synergistic toxic effect with Fludarabine. *Leukemia* 18, 1215-1222.
31. Baluna, R., Rizo, J., Gordon, B. E., Ghetie, V., and Vitetta, E. S. (1999) Evidence for a structural motif in toxins and interleukin-2 that may be responsible for binding to endothelial cells and initiating vascular leak syndrome. *Proc. Natl. Acad. Sci. USA* 96, 3957-3962.
32. Baluna, R., Coleman, E., Jones, C., Ghetia, V., and Vitetta, E. S. (2000) The Effect of a Monoclonal Antibody Coupled to Ricin A Chain-Derived Peptides on Endothelial Cells in Vitro: Insights into Toxin-Mediated Vascular Damage Exp. *Cell Res.* 258, 417-424.
33. Smallshaw, J. E., Ghetie, V., Rizo, J., Fulmer, J. R., Trahan, L. L, Ghetie, M. A., and Vitetta, E. S. (2003) Genetic engineering of an immunotoxin to eliminate pulmonary vascular leak in mice. *Nature Biotechnology* 27, 387-391
34. Barbieri, L., Valbonesi, P., Bonora, E., Gorini, P., Bolognesi, A., and Stirpe, F. (1997) Polynucleotide:adenosine glycosidase activity of ribosome-inactivating proteins: effect on DNA, RNA and poly(A). *Nucleic Acids Research* 25, 518-522.
35. Barbieri, L., Gorini, P. Valbonesi, P. Castiglioni, P., and Stirpe, F. (1994) Unexpected activity of saporins. *Nature (London)* 372, 624.

What is claimed is:

1. A transition state inhibitor of saporin-L1 selected from the group consisting of:

an inhibitor having the structure:

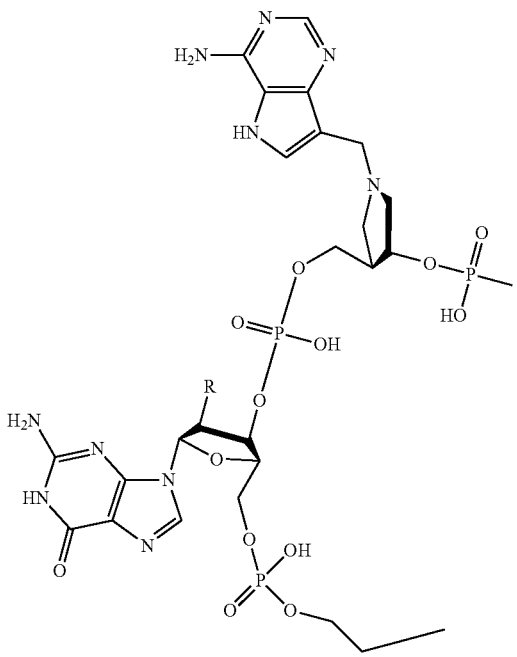

-continued

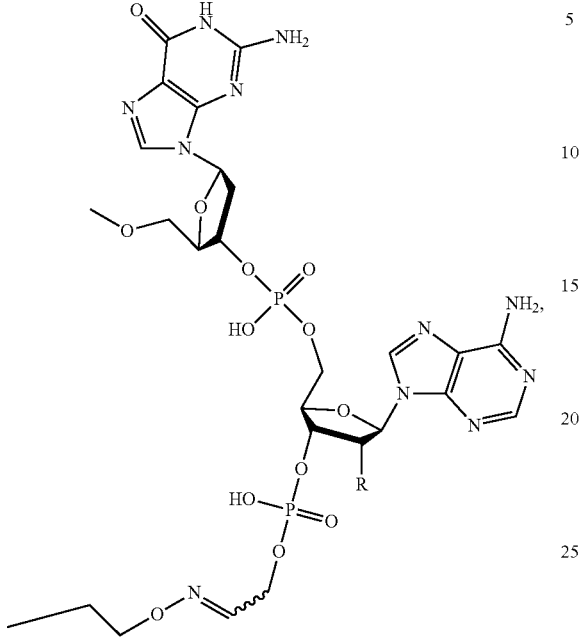

wherein each R is independently $OCH_3$ or aryl or alkyl, where the aryl or alkyl can be optionally substituted with one or more of OH, =O, $OCH_3$, $NH_2$, C1-C6 alkyl or halogen;

or a pharmaceutically acceptable salt thereof;

an inhibitor having the structure:

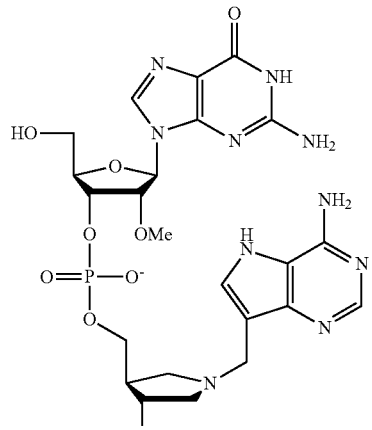

-continued

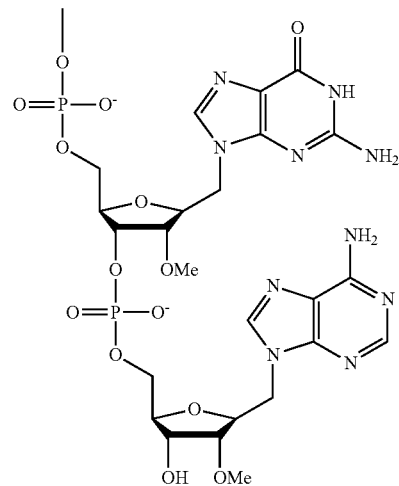

or a pharmaceutically acceptable salt thereof;
an inhibitor having the structure:

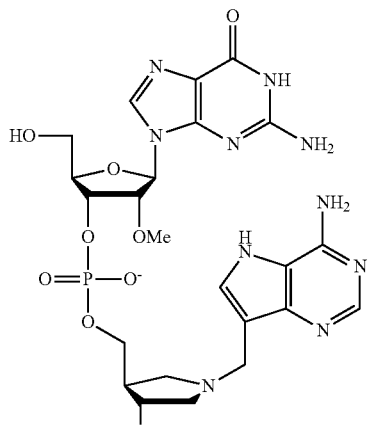

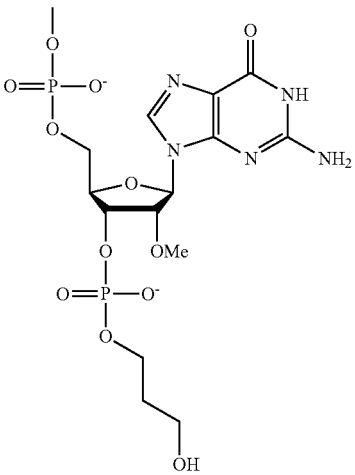

or a pharmaceutically acceptable salt thereof;

an inhibitor having the structure:
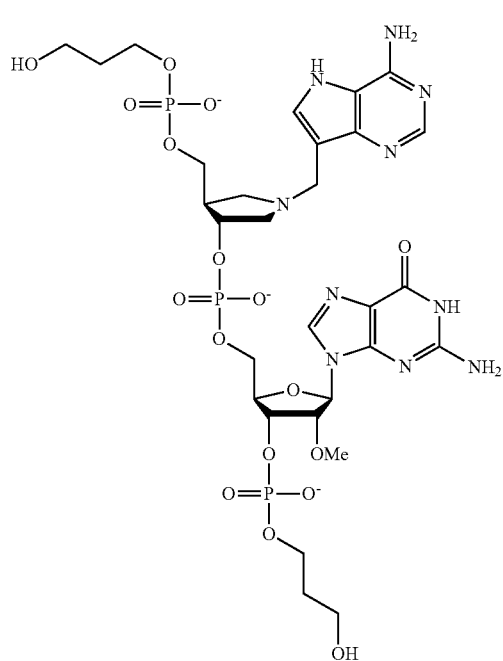
or a pharmaceutically acceptable salt thereof;
an inhibitor having the structure:
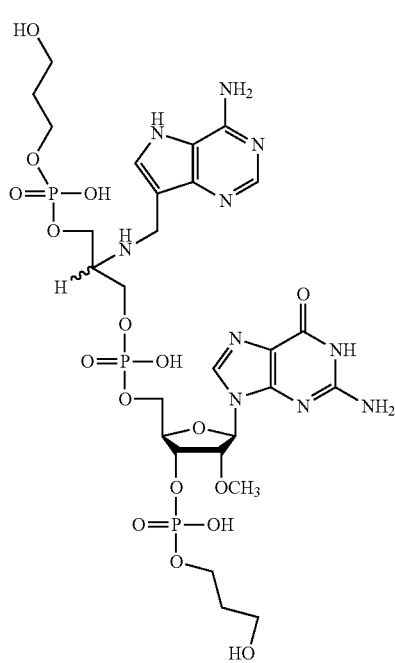
or a pharmaceutically acceptable salt thereof;
an inhibitor having the structure:
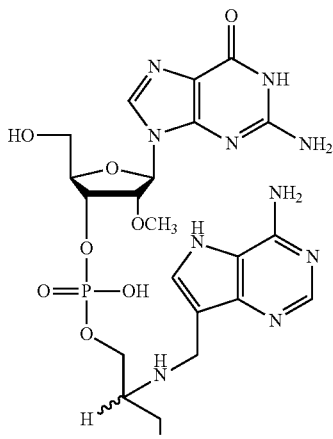
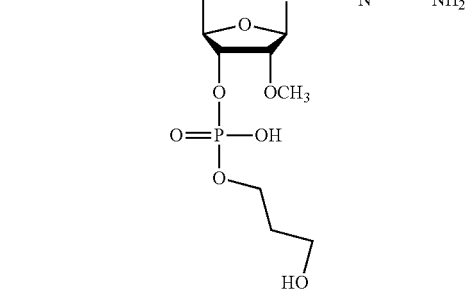
or a pharmaceutically acceptable salt thereof; and
an inhibitor having the structure:
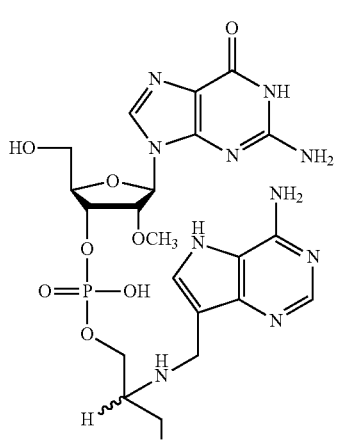

-continued

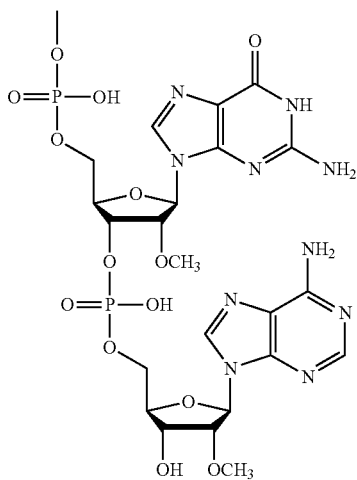

or a pharmaceutically acceptable salt thereof.

2. The inhibitor of claim 1 having the structure:

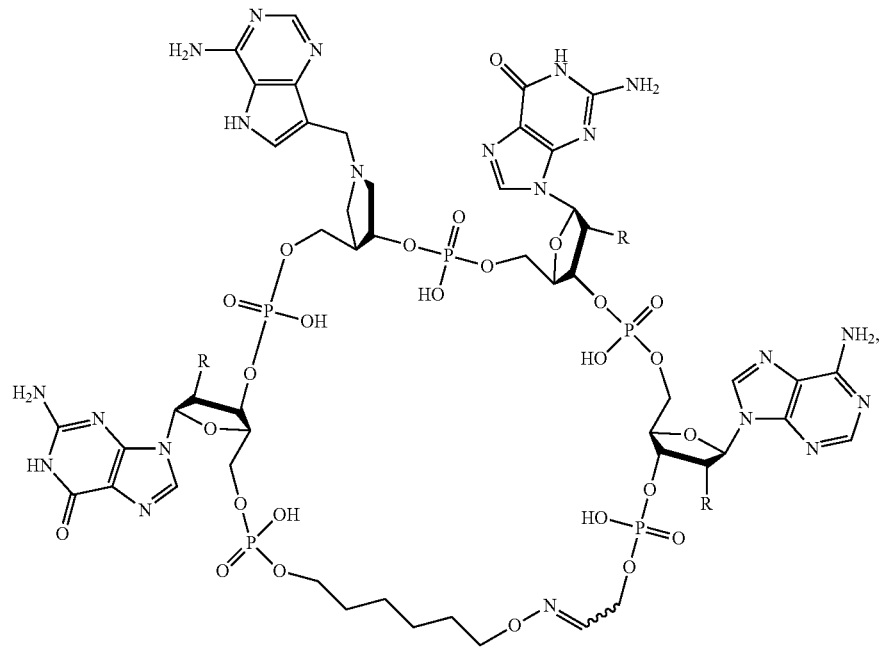

or a pharmaceutically acceptable salt thereof.

3. The inhibitor of claim 1, wherein R at one or more positions is $OCH_3$.

4. The inhibitor of claim 1, wherein R at one or more positions is aryl.

5. The inhibitor of claim 1, wherein R at one or more positions is alkyl.

6. The inhibitor of claim 1, wherein aryl is phenyl or phenyl substituted with one or more of —$CH_3$, —OH, —$OCH_3$, —F, —Cl, —Br, or —I.

7. The inhibitor of claim 1, wherein alkyl is C1-C6.

8. The inhibitor of claim 1 having the structure:

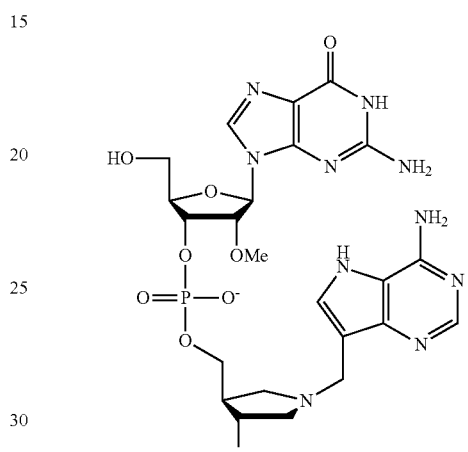

-continued
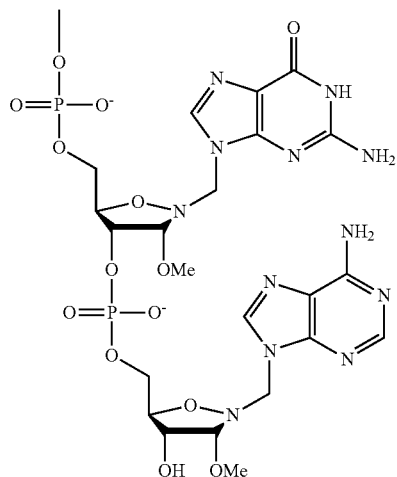
or a pharmaceutically acceptable salt thereof.
9. The inhibitor of claim 1 having the structure:
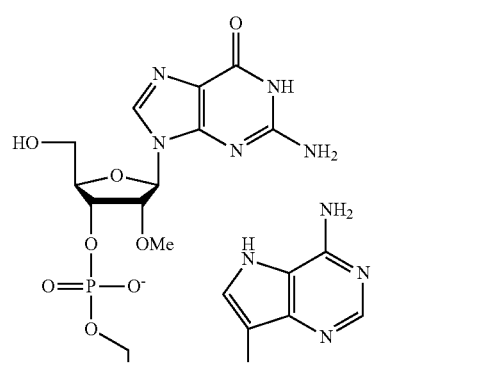
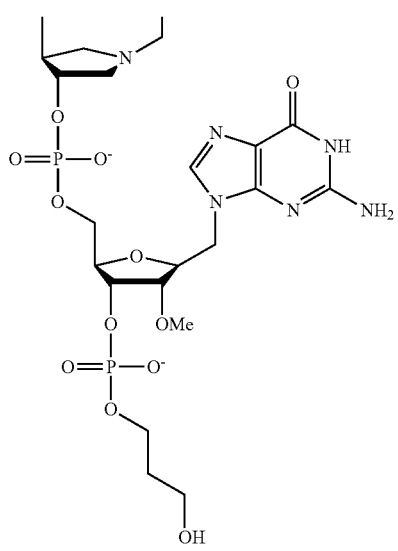
or a pharmaceutically acceptable salt thereof.
10. The inhibitor of claim 1 having the structure:
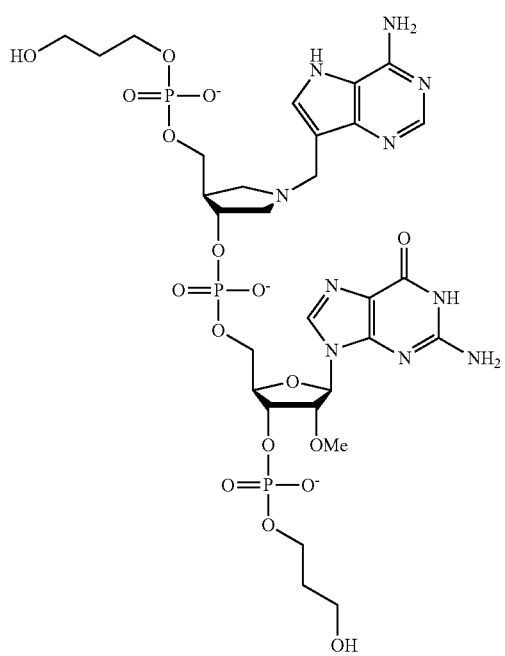
or a pharmaceutically acceptable salt thereof.
11. The inhibitor of claim 1 having the structure:
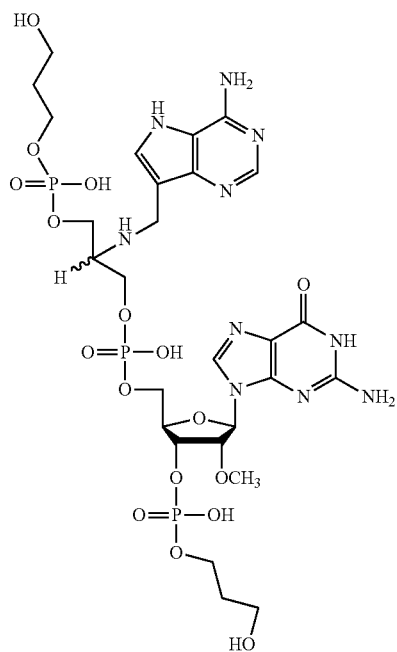
or a pharmaceutically acceptable salt thereof.

12. The inhibitor of claim 1 having the structure:

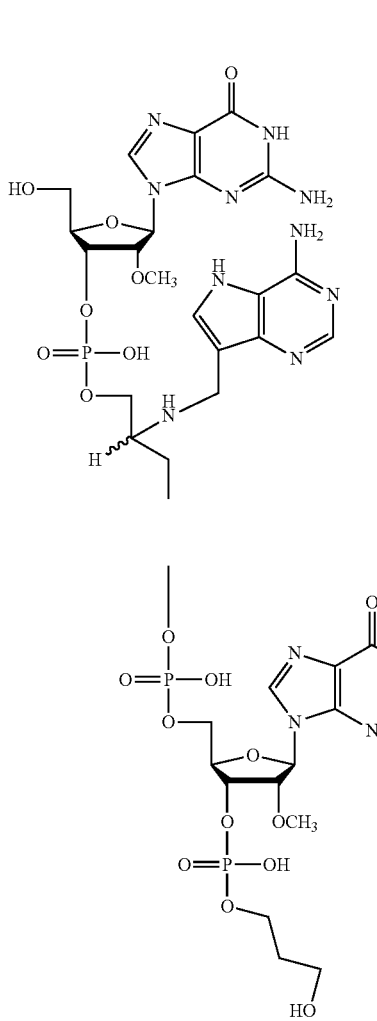

or a pharmaceutically acceptable salt thereof.

13. The inhibitor of claim 1 having the structure:

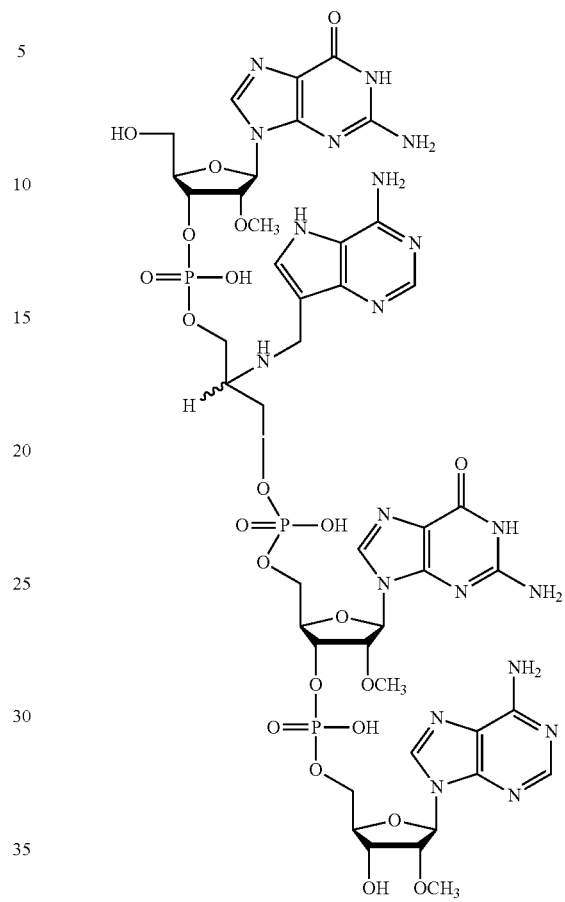

or a pharmaceutically acceptable salt thereof.

14. A pharmaceutical composition comprising the inhibitor of claim 1 and a pharmaceutically acceptable carrier.

15. A method for inhibiting the activity of saporin-L1 comprising contacting saporin -L1 with the inhibitor of claim 1.

16. The method of claim 15 carried out at a pH of 7.3-7.5.

* * * * *

SEQUENCE LISTING

<160> NUMBER OF SEQ ID NOS: 2

<210> SEQ ID NO 1
<211> LENGTH: 10
<212> TYPE: RNA
<213> ORGANISM: Artificial Sequence
<220> FEATURE:
<223> OTHER INFORMATION: stem-loop substrate

<400> SEQUENCE: 1
cgcgagagcg                                                          10

<210> SEQ ID NO 2
<211> LENGTH: 10
<212> TYPE: PRT
<213> ORGANISM: Saponaria officinalis

<400> SEQUENCE: 2

Val Ile Ile Tyr Glu Leu Asn Leu Gln Gly
1               5                   10